(12) United States Patent
Ben et al.

(10) Patent No.: US 10,758,565 B2
(45) Date of Patent: Sep. 1, 2020

(54) COMPOSITIONS OF AMORPHOUS CALCIUM CARBONATE FOR INHALATION, SUBLINGUAL OR BUCCAL ADMINISTRATION

(71) Applicant: AMORPHICAL LTD., Ness Ziona (IL)

(72) Inventors: Yosef Ben, Arava (IL); Yigal Dov Blum, San Jose, CA (US)

(73) Assignee: AMORPHICAL LTD., Ness Ziona (IL)

( * ) Notice: Subject to any disclaimer, the term of this patent is extended or adjusted under 35 U.S.C. 154(b) by 0 days.

(21) Appl. No.: 15/578,829

(22) PCT Filed: Jun. 2, 2016

(86) PCT No.: PCT/IL2016/050573
§ 371 (c)(1),
(2) Date: Dec. 1, 2017

(87) PCT Pub. No.: WO2016/193983
PCT Pub. Date: Dec. 8, 2016

(65) Prior Publication Data
US 2018/0153930 A1 Jun. 7, 2018

Related U.S. Application Data

(60) Provisional application No. 62/170,712, filed on Jun. 4, 2015.

(51) Int. Cl.
| | | |
|---|---|---|
| *A61K 31/00* | (2006.01) | |
| *A61K 33/10* | (2006.01) | |
| *A61K 9/00* | (2006.01) | |
| *A61K 9/14* | (2006.01) | |
| *A61P 35/00* | (2006.01) | |
| *A61K 47/24* | (2006.01) | |
| *A61K 9/10* | (2006.01) | |
| *A61P 31/00* | (2006.01) | |

(52) U.S. Cl.
CPC ............ *A61K 33/10* (2013.01); *A61K 9/0019* (2013.01); *A61K 9/0056* (2013.01); *A61K 9/0073* (2013.01); *A61K 9/10* (2013.01); *A61K 9/143* (2013.01); *A61K 47/24* (2013.01); *A61P 31/00* (2018.01); *A61P 35/00* (2018.01)

(58) Field of Classification Search
CPC ........ A61K 31/00; A61K 33/10; A61K 47/24; A61K 9/00; A61K 9/14; A61P 5/00
See application file for complete search history.

(56) References Cited

U.S. PATENT DOCUMENTS

| | | |
|---|---|---|
| 4,199,496 A | 4/1980 | Johnson |
| 5,437,857 A | 8/1995 | Tung |
| 8,728,533 B2 | 5/2014 | Ben |
| 8,802,160 B2 | 8/2014 | Bentov |
| 9,149,494 B2 | 10/2015 | Sagi |
| 9,550,878 B2 | 1/2017 | Meiron |
| 2008/0226715 A1 | 9/2008 | Cha |
| 2011/0313052 A1* | 12/2011 | Engqvist ............ A61K 9/0019 514/770 |
| 2013/0190441 A1 | 7/2013 | Vucak |

FOREIGN PATENT DOCUMENTS

| | | |
|---|---|---|
| CA | 2806131 | 2/2012 |
| CN | 101580260 | 11/2009 |
| CN | 101969962 | 2/2011 |
| CN | 103663532 B | 10/2015 |
| JP | H099871 | 1/1997 |
| JP | 2008500332 | 1/2008 |
| JP | 2008545845 A | 12/2008 |
| JP | 2011501676 | 1/2011 |
| KR | 1020050110119 | 11/2005 |
| WO | 9404460 A1 | 3/1994 |
| WO | 2005041921 | 5/2005 |
| WO | 2005115414 | 12/2005 |
| WO | 2008041236 | 4/2008 |
| WO | 2009053967 | 4/2009 |
| WO | 2010093285 A1 | 8/2010 |
| WO | 2012030664 A1 | 3/2012 |
| WO | 2012149173 | 11/2012 |
| WO | 2013088440 | 6/2013 |
| WO | 2014024191 | 2/2014 |
| WO | 2014122658 | 8/2014 |
| WO | 2016016893 | 2/2016 |
| WO | 2016016895 | 2/2016 |

OTHER PUBLICATIONS

Addadi et al., (2003) Taking advantage of disorder: amorphous calcium carbonate and its roles in biomineralization. Advanced Materials 15(12):959-970.
Amjad & Hooley, (1994) Effect of antiscalants on the precipitation of calcium carbonate in aqueous solutions. Tenside, surfactants, detergents, 31(1), 12-17.
Bentov et al., (2010) Stabilization of amorphous calcium carbonate by phosphate rich organic matrix proteins and by single phosphoamino acids. Journal of structural biology, 171(2), 207-215.
Buehrer & Reitemeier, (1940) The Inhibiting Action of Minute Amounts of Sodium Hexametaphosphate on the Precipitation of Calcium Carbonate from Ammoniacal Solutions. II. Mechanism of the Process, with Special Reference to the Formation of Calcium Carbonate Crystals. The Journal of Physical Chemistry, 44(5), 552-574.
Chen et al., (2013) Ethanol assisted synthesis of pure and stable amorphous calcium carbonate nanoparticles. Chemical Communications, 49(83), 9564-9566.
Database WPI Week 200432 Thomson Scientific, London, GB; AN 343036 XP002512142 & JP 2004 081739 A (Bankoku Needle MFG) Mar. 18, 2004 (Mar. 18, 2004) & JP 2004 081739 A (Akashi Mitsuru; Tabata Viasashi; Biomedical Technology Hybrid L) Mar. 18, 2004 (Mar. 18, 2004).

(Continued)

*Primary Examiner* — Zohreh A Fay
(74) *Attorney, Agent, or Firm* — Dorsey & Whitney LLP

(57) ABSTRACT

The present invention provides compositions comprising amorphous calcium carbonate (ACC), suitable to being administered by inhalation, and methods for their use in treating ACC-responsive diseases and conditions. Further provided are ACC compositions suitable for buccal or sublingual administration.

21 Claims, No Drawings

(56) References Cited

OTHER PUBLICATIONS

Gal et al., (1996) Calcium carbonate solubility: a reappraisal of scale formation and inhibition. Talanta, 43(9), 1497-1509.

Hecker et al., (2003) Phosphorylation of serine residues is fundamental for the calcium-binding ability of Orchestin, a soluble matrix protein from crustacean calcium storage structures. FEBS Lett 535(1-3): 49-54.

Huang et al., (2007) a carbonate controlled-addition method for amorphous calcium carbonate spheres stabilized by poly (acrylic acid) s. Langmuir, 23(24), 12086-12095.

Inoue et al., (2001) Purification and structural determination of a phosphorylated peptide with anti-calcification and chitin-binding activities in the exoskeleton of the crayfish, Procambarus clarkii. Biosci Biotechnol Biochem 65(8): 1840-1848.

Kavanagh et al., (1990) Inhibitor effects on calcite growth at low supersaturations. Journal of the Chemical Society, Faraday Transactions, 86(6), 965-972.

Lee et al., (2005) Fabrication of unusually stable amorphous calcium carbonate in an ethanol medium. Materials Chemistry and Physics 93(2-3): 376-382.

Lin & Singer, (2005) Inhibition of calcite crystal growth by polyphosphates. Water Research, 39(19), 4835-4843.

Meiron et al., (2011) Solubility and bioavailability of stabilized amorphous calcium carbonate. Journal of Bone and Mineral Research, 26(2), 364-372.

Occupational Safety and Health Administration (OSHA), 1995; Occupational Safety and Health Guideline for Calcium Carbonate. U.S. Department of Health and Human Services and U.S. Department of Labor; 7 pages.

Raz et al., (2002) Stable amorphous calcium carbonate is the main component of the calcium storage structures of the crustacean Orchestia cavimana. Biol Bull 203: 269-274.

Sawada, (1997) The mechanisms of crystallization and transformation of calcium carbonates. Pure and Applied Chemistry, 69(5), 921-928.

Schepers, (1959) Pulmonary histologic reactions to inhaled fiberglas-plastic dust. The American journal of pathology, 35(6), 1169-1187.

Shechter et al., (2008) A gastrolith protein serving a dual role in the formation of an amorphous mineral containing extracellular matrix. Proc Natl Acad Sci U S A 105(20): 7129-7134.

Sugawara et al., (2006) Self-organization of oriented calcium carbonate/polymer composites: Effects of a matrix peptide isolated from the exoskeleton of a crayfish. Angew Chem Int Ed Engl 45(18): 2876-2879.

Takagi et al., (2000) Immunolocalization of gastrolith matrix protein Science 17: 179-184.

Tlili et al., (2002) Characterization of $CaCO_3$ hydrates by micro-Raman spectroscopy. Journal of Raman spectroscopy, 33(1), 10-16.

Tolba et al., (2016) High biocompatibility and improved osteogenic potential of amorphous calcium carbonate/vaterite. Journal of Materials Chemistry B, 4(3), 376-386.

Travis (1960) The Deposition of Skeletal Structures in the Crustacea. I. The Histology of the Gastrolith Skeletal Tissue Complex and the Gastrolith in the Crayfish, Orconectes (Cambarus) Virllis Hagen—Decapoda. Biol Bull 118: 137-149.

Ueno and Mizuhira (1984) Calcium transport mechanism in crayfish gastrolith epithelium correlated with the molting cycle. II. Cytochemical demonstration of $Ca^{2+}$-ATPase and $Mg^{2+}$-ATPase. Histochemistry 80(3): 213-7.

Wolf & Günther, (2001) Thermophysical investigations of the polymorphous phases of calcium carbonate. Journal of thermal analysis and calorimetry, 65(3), 687-698.

Xurong et al., (2008) Amorphous Calcium Carbonate in Biomineralization. Progress in Chemistry 20(1): 54-59.

Qi et al., (2014) Atp-stabilized amorphous calcium carbonate nanospheres and their application in protein adsorption. Small 10(10): 2047-2056.

Xu et al., (2005) Stable amorphous $CaCO_3$ microparticles with hollow spherical superstructures stabilized by phytic acid. Advanced Materials 17(18): 2217-2221.

Sawada et al., (2003) Adsorption of inorganic phosphates and organic polyphosphonate on calcite. Dalton Trans 2003(3): 342-347.

Lin et al., (2015) Effects of Chalk Use on Dust Exposure and Classroom Air Quality. Aerosol and Air quality research 15: 2596-2608.

\* cited by examiner

COMPOSITIONS OF AMORPHOUS CALCIUM CARBONATE FOR INHALATION, SUBLINGUAL OR BUCCAL ADMINISTRATION

FIELD OF THE INVENTION

The present invention provides compositions comprising amorphous calcium carbonate (ACC) stabilized by at least one stabilizer, suitable to being administered by inhalation, by buccal or sublingual administration.

BACKGROUND OF THE INVENTION

Calcium is considered to be one of the most important minerals in the human body. It is required for maintaining bone mineral density, is essential for exocytosis of neurotransmitters, takes part in the contraction of muscle cells, replaces sodium as the depolarizing mineral in the heart, and participates in many other physiological functions.

Calcium used in supplements today, whether obtained from natural sources or synthetic precipitates, may comprise both organic and inorganic calcium salts. Calcium carbonate—an inorganic salt of calcium—is the main compound commercially used in the nutrient supplement market. Calcium carbonate has six known polymorphs, three of which are anhydrous crystalline (i.e., calcite, aragonite, and vaterite), two of which are hydrated (i.e., crystalline monohydrocalcite and ikaite), and one of which is hydrated amorphous, namely, amorphous calcium carbonate (ACC). The most thermodynamically stable of these phases is calcite, whereas the least stable is ACC. ACC is a form that precipitates out of a supersaturated solution, if not stabilized by any element or compound. ACC will crystallize rapidly and completely into one of the five more stable polymorphs within seconds. Solubility studies suggest dramatic differences between the calcium carbonate polymorphs. While crystalline phases are considered poorly soluble, the amorphous form is much more soluble.

In nature, ACC is utilized by a number of organisms, mainly crustaceans and other invertebrates that developed capabilities for stabilizing ACC in transient mineral deposition sites. These organisms require an exceptional efficient mineral source for the periodical mobilization, absorption and precipitation of calcium. In some crustaceans, such as the freshwater crayfish, ACC is stored in large quantities in specialized transient storage organs, named the gastrolith.

Various orally-administrable formulations comprising amorphous calcium carbonate have been disclosed. For example, International Patent Application published as WO 2005/115414 is directed to the use of the gastrolith organs, ground to a fine powder in pharmaceutical and nutraceutical calcium compositions. It was further disclosed that daily oral consumption of compositions comprising gastrolith components dramatically improves a range of conditions such as bone disorders, bone fractures, and cancer (WO 2008/041236). Pharmaceutical and nutraceutical compositions comprising ACC and phosphorylated peptides or amino acids for treating various disorders and conditions are disclosed in WO 2009/053967. The oral administration is, however, not always feasible or sufficient. There is a need for additional methods for administration of ACC.

SUMMARY OF THE INVENTION

The present invention provides compositions comprising amorphous calcium carbonate (ACC) as an active agent, formulated to be administered via inhalation, repositories comprising metered dose units of said compositions, inhalers comprising said repositories, and the use thereof in treating ACC-responsive diseases and conditions, including cancer. Also provided are compositions comprising ACC formulated for buccal and/or sublingual and gingival administration. The compositions formulated for inhalation and compositions formulated for buccal and/or sublingual and/or gingival administration can be administered separately or in combination with each other.

According to one aspect, the present invention provides a composition comprising an amorphous calcium carbonate (ACC) as an active agent, stabilized by at least one stabilizer, wherein the ACC is in the form of particles, and wherein the composition is formulated for administration mode selected from the group consisting of inhalation, buccal, sublingual and gingival administration.

According to some embodiments the ACC is natural ACC. According to another embodiment the ACC is a synthetic ACC stabilized by at least one stabilizer. According to some embodiments the stabilizer is selected from the group consisting of a polyphosphate, bisphosphonate, phosphorylated amino acid, citric acid, and any combination thereof.

According to some embodiments, the composition is a solid. According to one embodiment, the composition is in the form of a dry powder. Such dry powder, according to certain embodiments comprises less than 30 wt % water.

According to one embodiment the composition is formulated as a solid dispersion. Such a dispersion according to another embodiment further comprises a bulking agent.

According to another embodiment, the composition is formulated in the form of a suspension of ACC in a liquid carrier. According to some embodiment the liquid carrier is water, water for injection or saline. According to further embodiments, the ACC remains stable in such a suspension for at least 1 hour, 1 day, 7 days, 14 days, 1 month or at least 3 months.

Any composition according to the present invention may further comprise at least one additional active agent.

The composition according to the present invention is, in some embodiments, formulated for administration via inhalation. In some embodiments, at least 90% of the particle of ACC stabilized with at least one stabilizing agent of such composition have particle size of 20 µm or less. In other embodiments at least at least 90% of the particle have a particle size of 5 µm or less. According to some embodiments, the composition formulated for administration via inhalation is in the form of a dry powder configured for dry powder inhalation.

According another aspect the composition of the present invention is a pharmaceutical composition.

According to a further aspect the present invention provides a pharmaceutical composition comprising the composition of the present invention, and a pharmaceutically acceptable carrier, for use in treating a disease or a condition responsive to a calcium carbonate treatment, wherein said pharmaceutical composition is formulated for an administration mode selected from the group consisting of inhalation, buccal, gingival and sublingual administration. According to some embodiments the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious diseases and dental diseases.

In certain embodiments, the pharmaceutical composition is for use in treating pain via inhalation. In certain embodiments, the pharmaceutical composition is used for treating cancer or at least one symptom thereof via inhalation. In certain embodiments, the pharmaceutical composition is for use in the treatment of sarcomas, carcinomas, lymphomas and melanomas. Each possibility represents a separate embodiment of the invention. In some embodiments, the pharmaceutical composition is for use in the treatment of carcinoma. In some embodiments, said carcinoma is a carcinoma of lung. In some embodiments, said carcinoma is a breast carcinoma. In further embodiments, said breast carcinoma has metastases in other organs, including, but not limited to, lungs. In some embodiments, the pharmaceutical composition is for use in combination with orally administrable ACC.

According to some embodiments, the pharmaceutical composition of the present invention is formulated for administration via inhalation. According to some embodiments, the pharmaceutical composition is formulated as a suspension.

In another aspect, the present invention provides a repository comprising at least one metered dose of the pharmaceutical composition described above, packed in a packaging configured to be used with a dry powder inhaler.

In certain aspect, the present invention provides an inhaler comprising the repository of the present invention, configured to allow administration by inhalation of the at least one metered dose of the pharmaceutical composition. The repository comprising at least one metered dose of the pharmaceutical composition described above, packed in a packaging configured to be used with a dry powder inhaler.

In still another aspect the present invention provides a method of treating a disease or a condition responsive to a calcium carbonate treatment in a subject in need thereof, comprising administering to the subject an ACC stabilized by at least one stabilizer via a route of administration selected from administration via inhalation, buccal administration, sublingual administration, gingival administration and any combination thereof. According to some embodiments the method comprising administering to the subject the composition or the pharmaceutical composition of the present invention. According to some embodiments, the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious diseases and dental problems.

According to some embodiments the method comprising administering via inhalation a composition comprising 0.1 to 5% ACC stabilized by at least one stabilizer in a dose of about 8 ml.

According to another embodiment the dose of buccally and/or sublingually administered ACC is up to 2000 mg/day.

In a further aspect, the present invention provides use of a composition according to the present invention in the preparation of a medicament formulated for administration via an administration selected from administration via inhalation, buccal, sublingual and gingival administration, for treating a disease or a condition responsive to calcium a carbonate treatment.

DETAILED DESCRIPTION OF THE INVENTION

In one aspect, the present invention provides a composition comprising an amorphous calcium carbonate (ACC) as an active agent, stabilized by at least one stabilizer, wherein the ACC is in the form of particles, and wherein the composition is formulated for administration selected from the group consisting of administration via inhalation, buccal, sublingual and gingival administration.

The terms "amorphous calcium carbonate" and "ACC" are used herein interchangeably and refer to the amorphous and least stable polymorph of calcium carbonate.

The term "active agent" as used herein refers to any compound or mixture of compounds which produces a physiological result, e.g., a beneficial or useful result, upon contact with a living organism, e.g., a mammal, such as a human. Active agents are distinguishable from other components of the delivery compositions, such as carriers, diluents, lubricants, binders, colorants, etc. In some embodiments, the active agent is ACC. In some embodiments, the composition or the pharmaceutical composition includes a combination of ACC with an additional active agent. In certain embodiments, said additional active agent is bisphosphonate. In some embodiments, an active agent might also provide the function of another component of the delivery compositions, such as carriers, diluents, lubricants, binders, colorants, etc.

The term "particles" as used herein refers to a discrete microparticle or a nanoparticle of ACC stabilized by the stabilizer as defined hereinabove, as well as to the aggregates or agglomerates thereof. According to some embodiments, the particles are primary particles of the stabilized ACC. The basic nanoparticles are in the range of 5 to 500 nm or 10 to 300 nm or 20 to 100 nm. In many cases, these nanoparticles immediately agglomerate and aggregate into much larger secondary particles. These aggregation and agglomeration can be then broken by milling and dissolution techniques into smaller particles. According to other embodiments, the particles are agglomerates or aggregates of the primary particles, i.e. secondary particles.

The term "particle size" as used herein refers to a measurement of a representative diameter of the particle such as an aggregate in at least one dimension.

According to one embodiment the administration is selected from the group consisting of administration via inhalation, buccal, sublingual and gingival administration.

The terms "formulated for inhalation" and "inhalation formulation" as used herein interchangeably refer to any formulation which may be absorbed by the body when administered to the respiratory tract of a subject.

According to some embodiments the ACC is natural ACC. According to another embodiment the ACC is synthetic ACC.

The term "natural ACC" as used herein refers to any ACC isolated or derived from a natural source. Non-limiting examples of natural sources of ACC include gastroliths of freshwater crustaceans.

In certain embodiments, the ACC is produced from a naturally occurring ACC source. In certain embodiments, the naturally occurring ACC source includes gastrolith organs, or a portion thereof ground to a fine powder, essentially as described in WO 2005/115414, which is hereby incorporated by reference in its entirety. Optionally, ACC comprises a combination of naturally occurring and synthesized ACC.

The term "synthetic ACC" as used herein generally refers to any ACC produced by man ex-vivo.

In certain embodiments, the ACC is produced synthetically. According to any one of the above embodiments the ACC is stabilized by at least one stabilizer.

The term "stabilizer" as used herein refers to any substance that contributes to preserving calcium carbonate in the amorphous state thereof, during ACC production, formulating and/or storage. In certain embodiments the stabilizing agent may be a single agent. In other embodiments use of several stabilizing agents is encompassed.

ACC Stabilizers

The stabilizer may comprise a molecule having one or more functional groups selected from, but not limited to, hydroxyl, carboxyl, ester, amine, phosphino, phosphono, phosphate, sulfonyl, sulfate or sulfino groups. The hydroxy bearing compounds, combined with the hydroxide, optionally also bear other functions like carboxyl, etc. but with the hydroxyl not being esterified.

According to some embodiments the stabilizer has low toxicity or no toxicity to mammalian cells or organism, and in particular to a human being. According to some embodiment the stabilizer is of food, nutraceutical or pharmaceutical grade.

In certain embodiments the ACC stabilizing agent is independently at each occurrence, an organic acid; phosphorylated, phosphonated, sulfated or sulfonated organic compound; phosphoric or sulfuric ester of a hydroxyl carboxylic acid; an organoamine compound; an organic compound comprising a hydroxyl; an organophosphorous compound or a salt thereof; phosphorylated amino acids and derivatives thereof, a bisphosphonate compound; an organophosphate compound, an organophosphonate compound; an inorganic phosphorous acid, an organic compound having multiple functional groups as defined above; an inorganic phosphate and polyphosphate compound; an organic compound having a polyphosphate chain; an organic surfactant; a bio-essential inorganic ion; or any combination thereof.

According to some embodiments, the polyphosphate is physiologically compatible, water soluble polyphosphate salt selected from the group consisting of sodium, potassium and any other essential cation of polyphosphate. Non-limiting examples of polyphosphates include pyrophosphate, triphosphate, hexametaphosphate and combinations thereof. In one embodiment the polyphosphate is organic or inorganic polyphosphate.

Non-limiting examples of suitable bisphosphonates include etidronic acid, zoledronic acid, medronic acid and combinations thereof.

The organic acids may be selected from ascorbic, citric, lactic or acetic acid, oxalic acid, malonic acid, glutaconic acid, succinic acid, maleic acid, lactic acid, aconitic acid, and optionally include compounds having at least two carboxylic groups and molecular weight not larger than 250 g/mol, such as citric acid, tartaric acid, malic acid, etc.

In another embodiment, the phosphoric ester of hydroxyl carboxylic acids is a phosphoenolpyruvate. In another embodiment, the phosphoric or sulfuric esters of hydroxyl carboxylic acids comprise amino acids. Examples of such esters are phosphoserine, phosphothreonine, sulfoserine, sulfothreonine and phosphocreatine.

The hydroxyl bearing compounds combined with hydroxide may comprise, for example, mono-, di- tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment of the present invention.

Some specific unlimited examples for such ACC stabilizers that were approved for food consumption, found in natural food or in human beings, include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and hydroxyl bearing organic compounds, selected from mono-, di-, tri-, oligo- and polysaccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments of the invention, the stabilizer is an organic acid selected from monocarboxylic acid or multiple carboxylic acid, e.g. dicarboxylic acid or tricarboxylic acid. Each possibility represents a separate embodiment of the invention. The organic acid may be as defined above.

In some embodiments of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N; P or S in the phase of oxides; or N as ammonia or nitro groups.

Optionally ACC is stabilized by a combination of phosphoserine and citric acid.

The stabilized ACC may be stabilized by more than one stabilizers, e.g. two stabilizers. In some embodiments, the first stabilizer and the second stabilizer are similar. In other embodiments, the first stabilizer and the second stabilizer are different stabilizers. The first and the second stabilizers may be each independently as defined hereinabove. The stable ACC can comprise more than two stabilizers, wherein the stabilizers may be same or different. The stable ACC can comprise more than two stabilizers, wherein one or more stabilizers are added to the ACC during the formation and precipitation of the ACC;

According to some embodiments, the ACC is a synthetic ACC, and is stabilized by at least one stabilizer as defined hereinabove.

According to some embodiments the at least one stabilizer is selected from the group consisting of a polyphosphate, bisphosphonate, phosphorylated amino acid, citric acid, and any combination thereof. In some embodiments more than one stabilizers, e.g. 2, 3 or 4 stabilizers are added.

According to some embodiments the stabilizer is a polyphosphate or pharmaceutically acceptable salts thereof. Non-limiting examples of the term "polyphosphate" as used herein refers to polymeric esters of $PO_4$. According to some embodiments, the polyphosphate is physiologically compatible water soluble polyphosphate salt selected from the group consisting of sodium and potassium polyphosphate. In some embodiments the polyphosphate is an inorganic polyphosphate or pharmaceutically acceptable salts thereof. Not-limiting examples of such salt are Na, K, Mg, Mn and Zn. According to some embodiments the inorganic phosphate comprise 2 to 10 phosphate groups, e.g. 2, 3, 4, 5, 6, 7, 8, 9, or 10 phosphate group. According to some embodiments the polyphosphate is selected from pyrophosphate, triphosphate, and hexametaphosphate. According to one embodiment the stabilizer is pyrophosphate or pharmaceutically acceptable salts thereof such as sodium pyrophosphate. According to another embodiment the stabilizer is triphosphate or pharmaceutically acceptable salts thereof such as sodium triphosphate. The term "triphosphate" and "tripolyphosphate" are used herein interchangeably. According to a further embodiment the stabilizer is hexametaphosphate or a pharmaceutically acceptable salt thereof such sodium hexametaphosphate.

According to some embodiment the stabilizer is a bisphosphonate or pharmaceutically acceptable salts thereof. The not-limiting examples of salt are Na, K, Mg, Mn and Zn.

The term "bisphosphonate" as used herein refers to organic compounds having two phosphonate ($PO(OH)_2$) groups. The term further relates to compounds having a backbone of $PO_3$-organic-$PO_3$. Most typical is a series of bisphosphonates that are used as pharmaceuticals for treating osteoporosis. According to some embodiments the bisphosphonate is selected from the group consisting of ctidronic acid, zoledronic acid, medronic acid, alendronic acid and a pharmaceutically acceptable salt thereof. According to some embodiments the stabilizer is an etidronic acid or a pharmaceutically acceptable salt thereof. According to another embodiment the stabilizer is a zoledronic acid or a pharmaceutically acceptable salt thereof. According to a further embodiment the stabilizer is a medronic acid or a pharmaceutically acceptable salt thereof. According to certain embodiments the stabilizer is alendronic acid or a pharmaceutically acceptable salt thereof.

According to certain embodiments, the stabilizer is a phosphorylated amino acid. According to one embodiment the phosphorylated amino acid is phosphoserine. According to another embodiment the phosphorylated amino acid is phosphothreonine.

According to some embodiments the stabilizer is an organic acid. According to certain embodiments the organic acid is selected from ascorbic acid, citric acid, lactic acid, acetic acid, oxalic acid, malonic acid, glutaconic acid, succinic acid, maleic acid, lactic acid, aconitic acid, and optionally include compounds having at least two carboxylic groups and molecular weight not larger than 250 g/mol, such as citric acid, tartaric acid, malic acid, etc. According to one particular embodiment the stabilizer is citric acid.

According to some embodiments, the ACC composition comprises a combination of the stabilizers disclosed above.

According to some embodiments the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiment, the P:Ca molar ratio is about 1:25 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In another particular embodiment the P:Ca molar ratio is about 1:25 to about 1:5. According to some embodiments such polyphosphate is pyrophosphate, triphosphate, hexametaphosphate or a pharmaceutically acceptable salt thereof. According to another embodiments the bisphosphonate is alendronic acid, etidronic acid, zoledronic acid or medronic acid and the P:Ca molar ratio is as defined hereinabove.

According to some embodiments the calcium content (Ca content) of such compositions comprising polyphosphate or bisphosphonate as a stabilizer is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 to about 38. The terms "Ca content" and "calcium content" is used herein interchangeably and refer to the content of calcium of the ACC in the final composition.

In certain embodiments the P:Ca molar ratio is about 1:40 to about 1:1, and the Ca content is about 20 wt % to about 39 wt %. In some embodiments the molar ratio is 1:28 to about 1:3, and the Ca content is about 30 wt % to about 38 wt %. In another embodiment the molar ratio is 1:25 to about 1:5, and the Ca content is about 30 wt % to about 36 wt %.

According to some embodiments, the ACC is natural ACC.

According to any one of the above embodiments, the composition is solid. According to another embodiment such composition is in the form of dry powder.

According to one embodiment the composition of the present invention is in the form of a dry powder, formulated for administration via inhalation, buccal, sublingual or gingival administration, comprises a stabilizer selected from the group consisting of polyphosphate, such as pyrophosphate, triphosphate and hexametaphosphate; bisphosphonate, such as alendronic acid, etidronic acid, zoledronic acid and medronic acid; phosphoserine; phosphothreonine; citric acid; and any combination thereof. In one embodiment the composition comprises polyphosphate or bisphosphonate, as defined herein, as a stabilizer and have the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In other embodiment, the P:Ca molar ratio is about 1:25 to about 1:4. In another particular embodiment the P:Ca molar ratio is about 1:25 to about 1:5. In further embodiments, the Ca content of such compositions is about 20 wt % to 39 wt %, about 30% to about 38%, about 32 wt % to about 38 wt % or about 30 wt % to about 36 wt %. In certain embodiments the P:Ca molar ratio is about 1:40 to about 1:1, and the Ca content is about wt % 20 wt % to about 38 wt %. In some embodiments the molar ratio is 1:28 to about 1:3, and the Ca content is about 30 wt % to about 38 wt %.

According to one embodiment the composition of the present invention is in the form of a dry powder and the ACC is natural ACC.

According to some embodiments the water content of the dry powder does not exceed 30%. Thus in some embodiments, the water content of the dry powder is less than 20% w/w, less than 15% w/w or less than 10% w/w. In some embodiments the dry powder composition comprises less than 5% water. In other embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 25 wt % water. In certain embodiments, the composition described above is a dry powder comprising 1 to 99% ACC by weight.

According to any one of the above embodiment the composition is stable.

The term "stable" is used herein to indicate that the calcium carbonate remains in the amorphous state for a period of time, for example for about at least 7 days in the solid form having less than or about 30% crystalline calcium carbonate. In some embodiments the ACC does not crystallize at all. According to other embodiments some of the ACC converts to a crystalline calcium carbonate. In some embodiments no more than 30% of ACC converts into the crystalline form and thus the composition comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate. According to some embodiment, the composition is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

According to some embodiments the composition according to any one of the above embodiments is in the form of a solid dispersion or a suspension.

The term "solid dispersion" as used herein refers to the solid composition of the present invention in an inert carrier or matrix at solid state and includes solid mixture systems.

The term "suspension" as used herein refers to a composition of solid particles dispersed in a liquid carrier.

The terms "liquid carrier" and "aqueous carrier" as used herein interchangeably refer to the aqueous vehicle in which the active agent e.g. ACC to be administered is suspended. Non-limiting examples of aqueous carrier include water and water based solutions (e.g. saline).

In one embodiments the composition is in the form of a solid dispersion. Such a composition comprises the solid composition of the present invention, e.g. a composition in the form of a powder, and further comprises a bulking agent.

The term "bulking agent" as used herein refers to one or more ingredients that can be combined with one or more active agents described herein (i.e., ACC) to increase the ease in which the active agent can be handled, measured and/or administered. Optionally the bulking agent has particles having similar size and weight properties to the active agent or ACC composition. In one embodiment the bulking agent is inert inhalable.

According to some embodiments, the solid dispersion comprises about 1 wt % to about 99 wt % of the ACC stabilized by at least one stabilizer, as defined hereinabove. According to other embodiments the solid dispersion comprises about 5 wt % to about 95 wt % of the ACC. According to other embodiments the solid dispersion comprises about 10 wt % to about 90 wt % of the ACC. According to other embodiments the solid dispersion comprises about 15 wt % to about 85 wt % of the ACC. According to other embodiments the solid dispersion comprises about 20 wt % to about 80 wt % of the ACC. According to other embodiments the solid dispersion comprises about 25 wt % to about 75 wt % of the ACC. According to other embodiments the solid dispersion comprises about 30 wt % to about 70 wt % of the ACC. According to other embodiments the solid dispersion comprises about 35 wt % to about 65 wt % of the ACC. According to other embodiments the solid dispersion comprises about 40 wt % to about 60 wt % of the ACC. According to other embodiments the solid dispersion comprises about 45 wt % to about 55 wt % ACC.

According to one embodiment, the composition is in the form of a suspension of the ACC in a liquid carrier.

According to some embodiments, the liquid carrier comprises at least 80 wt % water. In certain embodiments, the liquid carrier comprises at least 85% water by weight. In certain embodiments, the liquid carrier comprises at least 90% water by weight. In certain embodiments, the liquid carrier comprises at least 95% water by weight or even up to 99.9% water by weight. Optionally the liquid carrier is a philological saline, or any other acceptable pharmaceutical composition for inhalation.

According to one embodiment, the ACC of the composition in the form of a suspension remains stable for at least 1 hour. According to other embodiments the ACC of the composition in the form of a suspension remains stable for at least 1, 7, 14 days, 1, 3 or 6 months. According to one embodiment the ACC of the composition in the form of a suspension remains stable for at least 1 day. According to another embodiment, the composition is stable for at least 2 or 3 day. According to a further embodiment, the ACC of the composition in the form of a suspension remains stable for at least 7 days. According to certain embodiments, the ACC of the composition in the form of a suspension remains stable for at least 14 days. According to yet another embodiment, the ACC of the composition in the form of a suspension remains stable for at least 1 month. According to some embodiments, the ACC of the composition in the form of a suspension remains stable for at least 3 months.

According to some embodiments the composition in the form of a suspension as defined hereinabove comprises about 0.01 wt % to about 40 wt % w/w of ACC stabilized by at least one stabilizer. In further embodiments, the composition in the form of a suspension comprises from about 0.1 wt % to about to about 30 wt % of the ACC. According to another embodiment the composition in the form of a suspension comprises about 1 wt % to about 15 wt %, about 2 wt % to about 10 wt % or about 1 wt % to about 5 wt % of the ACC. In certain embodiments, the suspension comprises about 1% of the ACC. According to some other embodiments the composition in the form of a suspension comprises at least 0.1 wt %, at least 1 wt %, at least 5 wt % or at least 10 wt % of the ACC.

According to any one of the above embodiments, the composition may further comprise at least one additional active agent.

According to any one of the above embodiments, the composition is formulated for administration via inhalation. Examples for such formulations are solids, suspension, solid dispersion, a dry powder or acrosolizable suspension.

According to some embodiment the composition is formulated for administration via inhalation and the ACC is natural ACC.

According to some embodiment the composition is formulated for administration via inhalation and the ACC is a synthetic ACC.

Thus, according to one embodiment the composition according to the present invention comprising ACC stabilized by at least one stabilizer selected from the group consisting of polyphosphate, such as pyrophosphate, triphosphate and hexametaphosphate; bisphosphonate, such as alendronic acid, etidronic acid, zoledronic acid and medronic acid; phosphoserine; phosphothreonine; an organic acid with multiple functionalities such as citric acid, and any combination thereof, and the composition is formulated for administration via inhalation administration. According to some embodiments such composition formulated for administration via inhalation comprises as a stabilizer a polyphosphate. In one embodiment the polyphosphate is inorganic polyphosphate such as pyrophosphate, triphosphate or hexametaphosphate. According to some embodiments ACC is stabilized by any combination of said stabilizers.

According to some embodiments such composition formulated for administration via inhalation comprises as a stabilizer a bisphosphonate. In other embodiments the bisphosphonate is selected from alendronic acid, etidronic acid, zoledronic acid and medronic acid.

In one embodiment the composition formulated for administration via inhalation comprises polyphosphate or bisphosphonate, as defined herein, as a stabilizer as, and the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In other embodiment, the P:Ca molar ratio is about 1:28 to about 1:4. In another particular embodiment the P:Ca molar ratio is about 1:25 to about 1:5.

In further embodiments, the Ca content of the composition formulated for administration via inhalation is about 20 wt % to 39 wt %, about 30% to about 38%, about 32 wt % to about 38 wt % or about 30 wt % to about 36 wt %. In certain embodiments the P:Ca molar ratio is about 1:40 to about 1:1, and the Ca content is about wt % 20 wt % to about 38 wt %. In some embodiments the molar ratio is 1:28 to about 1:3, and the Ca content is about 30 wt % to about 38 wt %. In another embodiment the molar ratio is 1:25 to about 1:5, and the Ca content is about 30 wt % to about 36 wt %.

According to some embodiments the composition formulated for administration via inhalation comprises ACC stabilized by a phosphorylated amino acid. According to further embodiment the stabilizer is phosphoserine. According to further embodiment the stabilizer is phosphothreonine.

According to yet another embodiment the composition formulated for administration via inhalation comprise ACC stabilized by an organic acid with multiple binding functionalities. According to one embodiment the composition comprise ACC stabilized by citric acid.

According to some embodiments such composition formulated for administration via inhalation administration is solid as defined herein above. In particular embodiment the composition is in the form of a dry powder. According to some embodiments the water content of the dry powder does not exceed 30%. In some embodiment the water content of the dry powder is less than 20% w/w, less than 15% w/w or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 25 wt % water.

According to some embodiments the composition, and in particular solid composition, formulated for administration via inhalation is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

According to some embodiments, the composition formulated for administration via inhalation administration comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate.

According to some embodiments the composition formulated for administration via inhalation administration is in the form of a solid dispersion or suspension as defined herein above. In one embodiment the composition is in the form of a solid dispersion. Such a composition comprises the solid composition of the present invention, e.g. a composition in the form of a powder, and further comprises a bulking agent.

In another embodiment the composition formulated for administration via inhalation is in the form of a suspension of the solid composition according to the present invention in a liquid carrier as defined hereinabove. According to some embodiments the ACC in the composition in the form of a suspension remains stable for at least 1 hour, least 1, 7, 14 days, 1, 3 or 6 months.

According to some embodiments the composition for administration via inhalation administration further comprises at least one additional active agent.

As defined hereinabove the ACC stabilized by at least one stabilizer of the composition formulated for administration via inhalation is in the form of particles. According to some embodiments the particles are primary particles.

In certain embodiments, at least 70% of the particles of the composition have a particle size of 20 μm or less. In certain embodiments, at least 80% of the particles have a particle size of 20 μm or less. In certain embodiments, at least 90% of the particles have a particle size of 20 μm or less. In certain embodiments, at least 95% of the particles have a particle size of 20 μm or less.

In certain embodiments, at least 70% of the particles have a particle size of 15 μm or less. In certain embodiments, at least 80% of the particles have a particle size of 15 μm or less. In certain embodiments, at least 90% of the particles have a particle size of 15 μm or less. In certain embodiments, at least 95% of the particles have a particle size of 15 μm or less.

In certain embodiments, at least 70% of the particles have a particle size of 10 μm or less. In certain embodiments, at least 80% of the particles have a particle size of 10 μm or less. In certain embodiments, at least 90% of the particles have a particle size of 10 μm or less. In certain embodiments, at least 95% of the particles have a particle size of 10 μm or less.

In certain embodiments, at least 70% of the particles have a particle size of 5 μm or less. In certain embodiments, at least 80% of the particles have a particle size of 5 μm or less. In certain embodiments, at least 90% of the particles have a particle size of 5 µm or less. In certain embodiments, at least 95% of the particles have a particle size of 5 µm or less.

In certain embodiments, at least 80% of the particles have a particle size of 10-20 µm or less. In certain embodiments, at least 90% of the particles have a particle size of 10-20 µm or less. In certain embodiments, at least 80% of the particles have a particle size of 5-10 µm or less. In certain embodiments, at least 90% of the particles have a particle size of 5-10 µm or less.

According to some embodiments the composition formulated for administration via inhalation is in the form of a dry powder configured for dry powder inhalation.

ACC for dry powder inhalation is a dry powder comprising ACC having particle size that is less than 10 µm or even less than 5 µm for at least 90% of the particles.

Preparation of ACC for dry powder inhalation can be performed by drying caked matter produced as described hereinbelow, and milling it to reach the desired particle size. Other known methods for preparing ACC formulations may also be applied. Optionally, ACC is prepared by drying and milling naturally occurring ACC (for example a crustacean gastrolith).

According to the principles of the present invention, the powder comprises 1-99 wt % ACC. In some embodiments the powder is provided as a plurality individually packed single doses (e.g. 100-500 mg ACC per dose or 200-300 mg ACC/dose) insulated from external humidity. For example, the doses may be provided as capsules that are to be opened (e.g. cut or broken) to release the powder for use. Optionally the powder comprises a bulking agent (e.g. lactose) and is stored in a sealed container. Optionally, the powder comprises additives to prevent agglomerations. Optionally, the powder comprises a lubricating agent to aid the delivery of the powder during the inhalation operation. Optionally all components in the powder are inhalable, having a particle size of less than 20 µm or even less than 10 µm for at least 90% of the particles.

According to some embodiments the composition in the form of a suspension as defined hereinabove is formulated for inhalation. Such a composition is a water based suspension comprising particles of ACC stabilized by at least on stabilizer and having particle size that is less than 10 µm or even less than 5 µm for at least 90% of the particles. Optionally, the suspension includes an ACC/water w/w ratio of between 0.01% to 20%.

Preparation of ACC for suspension inhalation can be performed by suspending one or more of the aforementioned ACC powders in a volume of water, water for injection or saline.

Optionally, the ACC particles may be collected at any time after ACC is formed but before drying and suspended without drying. In such a case the suspension or caked ACC are milled.

Optionally, the ACC is provided in a dry form and is suspended in water before use.

According to any one of the above embodiments the composition further comprise one or more secondary stabilizer in addition to the stabilizer as defined above. Such additional stabilizers can be organic compounds known to serve as stabilizers for ACC, e.g., organic compounds containing carboxylic, amine, phosphate, phosphonate and other functional groups that tend to bond, chelate, or complexate to Ca ions like citric acid, lactate, phosphoserine, gluconate, etc. According to some embodiments the secondary stabilizer is as the first stabilizer.

According to certain embodiments the composition according to the present invention comprising ACC stabilized by at least one stabilizer selected from the group consisting of polyphosphate, such as pyrophosphate, triphosphate and hexametaphosphate; bisphosphonate, such as alendronic acid, etidronic acid, zoledronic acid and medronic acid; phosphoserine; phosphothreonine; citric acid; and any combination thereof, wherein said ACC is in the form of particles of which at least 90% of the particles have a particle size of 10 µm or less and composition is formulated for administration via inhalation. According to some embodiments the particles have a particle size of 5 µm or less. According to some embodiments the water content of the dry of the dry powder does not exceed 30%. In some embodiment the water content of the dry powder is less than 20% w/w, less than 15% w/w or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 25 wt % water. According to one embodiment such composition is in the form of a suspension in an aqueous carrier formulated for administration for inhalation or in the form of a solid dispersion comprising a bulking agent. According to one embodiment such composition is in the form of a suspension in aqueous carrier formulated for administration for inhalation or in the form of a solid dispersion comprising a bulking agent.

According to certain embodiments the composition according to the present invention is a solid composition in the form of a dry powder comprising ACC stabilized by pyrophosphate, triphosphate or hexametaphosphate; wherein said ACC is in the form of particles of which at least 90% of the particles have a particle size of 10 µm or less and composition is formulated for administration via inhalation and have the P:Ca molar ratio of about 1:25 to about 1:3. According to some embodiments the particles have a particle size of 5 µm or less. In other embodiment, the P:Ca molar ratio is about 1:25 to about 1:4. In further embodiment the P:Ca molar ratio is about 1:20 to about 1:5. In another particular embodiment the P:Ca molar ratio is about 1:25 to about 1:5. In further embodiments, the Ca content of such compositions is about 20 wt % to 38 wt %, or about 30 wt % to about 38 wt %. In certain embodiments the P:Ca molar ratio is about 1:25 to about 1:3, and the Ca content is about 30 wt % to about 38 wt %. In some embodiments the molar ratio is 1:28 to about 1:3, and the Ca content is about 30 wt % to about 38 wt %. In some embodiment the water content of the dry powder is less than 20% w/w, less than 15% w/w or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 20 wt % water. According to one embodiment such composition is in the form of a suspension in aqueous carrier formulated for administration for inhalation or in the form of a solid dispersion comprising a bulking agent.

According to certain embodiments, the composition according to the present invention is a solid composition in the form of a dry powder, comprising ACC stabilized by phosphoserine; wherein said ACC is in the form of particles of which at least 90/o of the particles have a particle size of 10 μm or less and composition is formulated for administration via inhalation. According to some embodiments the particles have a particle size of 5 μm or less. In some embodiment the water content of the dry powder is less than 20% w/w, less than 15% why or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 20 wt % water. According to one embodiment such composition is in the form of a suspension in aqueous carrier formulated for administration for inhalation or in the form of a solid dispersion comprising a bulking agent.

According to certain embodiments the composition according to the present invention is a solid composition in the form of a dry powder comprising ACC stabilized by etidronic acid, zoledronic acid or medronic acid, wherein said ACC is in the form of particles of which at least 90% of the particles have a particle size of 10 μm or less and composition is formulated for administration via inhalation and have the P:Ca molar ratio is about 1:25 to about 1:3. According to some embodiments the particles have a particle size of 5 μm or less. In other embodiment, the P:Ca molar ratio is about 1:25 to about 1:4. In further embodiment the P:Ca molar ratio is about 1:20 to about 1:5. In another particular embodiment the P:Ca molar ratio is about 1:25 to about 1:5. In further embodiments, the Ca content of such compositions is about 20 wt % to 39 wt % or about 30 wt % to about 38 wt %. In certain embodiments the P:Ca molar ratio is about 1:30 to about 1:3, and the Ca content is about 30 wt % to about 38 wt %. In some embodiments the molar ratio is 1:28 to about 1:3, and the Ca content is about 30 wt % to about 38 wt %. In some embodiment the water content of the dry powder is less than 20% w/w, less than 15% w/w or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 25 wt % water. According to one embodiment such composition is in the form of a suspension in aqueous carrier formulated for administration for inhalation or in the form of a solid dispersion comprising a bulking agent.

According to certain embodiments the composition according to the present invention is a solid composition in the form of a dry powder, comprising ACC stabilized by phosphoserine, wherein said ACC is in the form of particles of which at least 90% of the particles have a particle size of 5 μm or less, composition is formulated for administration via inhalation, and the water content of the dry powder is less than 20% w/w. In some embodiment the water content of the dry powder is less than 15% w/w or less than 10% w/w. In some embodiments the dry powder composition comprises about 5 wt % to about 20 wt % or about 5% to about 15 wt % water. According to another embodiment, the composition comprises about 10 wt % to about 20 wt % water. According to one embodiment such composition is in the form of a suspension in aqueous carrier formulated for administration for inhalation or in the form of a solid dispersion comprising a bulking agent.

According to certain embodiments the composition according to the present invention is a solid composition in the form a dry of powder, comprising ACC stabilized by triphosphate, wherein said ACC is in the form of particles of which at least 90% of the particles have a particle size of 5 μm or less, the water content of the dry powder is less than 20% w/w, the P:Ca molar ratio is about 1:25 to about 1:3, and the composition is formulated for administration via inhalation. In other embodiment, the P:Ca molar ratio is about 1:25 to about 1:4. According to certain embodiments the composition according to the present invention is a solid composition in the form of a dry powder, comprising ACC stabilized by hexametaphosphate, wherein said ACC is in the form of particles of which at least 90% of the particles have a particle size of 5 μm or less, the water content of the dry powder is less than 20% w/w, the P:Ca molar ratio is about 1:25 to about 1:3, and the composition is formulated for administration via inhalation. According to certain embodiments the composition according to the present invention is a solid composition in the form of a dry powder, comprising ACC stabilized by pyrophosphate, wherein said ACC is in the form of particles of which at least 90% of the particles have a particle size of 5 μm or less, the water content of the dry powder is less than 20% w/w, the P:Ca molar ratio is about 1:25 to about 1:3, and the composition is formulated for administration via inhalation. In other embodiment, the P:Ca molar ratio is about 1:25 to about 1:4. In further embodiment the P:Ca molar ratio is about 1:20 to about 1:5. In another particular embodiment the P:Ca molar ratio is about 1:25 to about 1:5. In further embodiments, the Ca content of such compositions is about 30 wt % to about 38 wt. In certain embodiments the P:Ca molar ratio is about 1:30 to about 1:3, and the Ca content is about 30 wt % to about 38 wt %. In some embodiments the molar ratio is 1:28 to about 1:3, and the Ca content is about 30 wt % to about 38 wt %. In some embodiments the dry powder composition comprises about 5 wt % to about 20% or about 5% to about 15 wt % water. According to another embodiment, the composition comprises about 10 wt % to about 20 wt % water. According to one embodiment such composition is in the form of a suspension in aqueous carrier formulated for administration for inhalation or in the form of a solid dispersion comprising a bulking agent.

According to any one of the above embodiments the composition formulated for administration via inhalation is in the form of a dry powder configured for dry powder inhalation.

According to any one of the above embodiments, the composition is formulated for buccal sublingual or gingival administration.

According to any one of the above embodiments, the composition is formulated for buccal administration.

As used herein, the terms "buccal delivery" or "buccal administration" mean delivery of a composition to a user by administration thereof to the mouth and retention of the composition in the buccal cavity for a period of time long enough for allowing at least some of the composition absorbed by buccal tissue. Examples include placing a composition in the form of powder or gel or liquid or semi-solid or solid form in the buccal cavity. Optionally, after a period of time (e.g. between 30 seconds-10 minutes, for example abut 3-6 minutes), any remaining material in the mouth may be discarded or swallowed by the user with or without the addition of, for example, a liquid (e.g. water).

Examples for compositions formulated for buccal administrations are adhesive tablets, patches, lozenges, gels, disks, wafers, and lamellae.

According to some embodiment the composition is formulated for buccal administration and the ACC is natural ACC.

According to some embodiment the composition is formulated for buccal administration and the ACC is synthetic ACC.

As used herein, the term "sublingual" means literally "under the tongue" and refers to a method of administering substances via the mouth in such a way that substances are rapidly absorbed under the tongue rather than via the digestive tract.

According to some embodiments the composition for sublingual administration may be formulated as tablets, strips, drops, spray or lozenges.

According to any one of the above embodiments, the composition is formulated for sublingual administration.

According to some embodiments, the composition is formulated for sublingual administration and the ACC is natural ACC.

According to some embodiments, the composition is formulated for sublingual administration and the ACC is synthetic ACC.

Thus according to one embodiment the composition according to the present invention comprising ACC stabilized by at least one stabilizer selected from the group consisting of polyphosphate, such as triphosphate, pyrophosphate and hexametaphosphate; bisphosphonate, such as alendronic acid, etidronic acid, zoledronic acid and medronic acid; phosphoserine; phosphothreonine; citric acid; and any combination thereof, and the composition is formulated for buccal, sublingual or gingival administration. According to some embodiments such composition formulated for buccal, sublingual or gingival administration comprises as a stabilizer a polyphosphate. In one embodiment the polyphosphate is inorganic polyphosphate such as pyrophosphate, triphosphate or hexametaphosphate.

According to some embodiments such composition formulated for buccal, sublingual or gingival administration comprises as a stabilizer a bisphosphonate. In other embodiments the bisphosphonate is selected from alendronic acid, etidronic acid, zoledronic acid and medronic acid.

In one embodiment the composition formulated for buccal, sublingual or gingival administration comprises polyphosphate or bisphosphonate, as defined herein, as a stabilizer as, and the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In other embodiment, the P:Ca molar ratio is about 1:28 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In certain embodiments the P:Ca molar ratio is about 1:25 to about 1:1. In another particular embodiment the P:Ca molar ratio is about 1:25 to about 1:5.

In further embodiments, the Ca content of composition formulated for buccal, sublingual or gingival administration is about 20 wt % to 38 wt %, about 30 wt % to about 38 wt %, about 32 wt % to about 38 wt % or about 30 wt % to about 36 wt %. In certain embodiments the P:Ca molar ratio is about 1:40 to about 1:1, and the Ca content is about wt % 20 wt % to about 38 wt %. In some embodiments the molar ratio is 1:28 to about 1:3, and the Ca content is about 30 wt % to about 38 wt %. In another embodiment the molar ratio is 1:25 to about 1:5, and the Ca content is about 30 wt % to about 36 wt %.

According to some embodiments the composition formulated for buccal, sublingual or gingival administration comprises ACC stabilized by a phosphorylated amino acid. According to further embodiment the stabilizer is phosphoserine. According to further embodiment the stabilizer is phosphothreonine.

According to yet another embodiment, the composition formulated for buccal, sublingual or gingival administration comprise ACC stabilized by citric acid.

According to some embodiments such composition formulated for buccal, sublingual or gingival administration is solid as defined herein above. In particular embodiment the solid composition is in the form of a dry powder. According to some embodiments the water content of the dry powder does not exceed 30%. In some embodiment the water content of the dry powder is less than 20% w/w, less than 15% w/w or less than 10% w/w. In some embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 25 wt % water.

According to some embodiments the composition, and in particular solid composition, formulated for buccal, sublingual or gingival administration is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

According to some embodiments, the composition formulated buccal, sublingual or gingival administration comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate.

According to some embodiments composition formulated for buccal, sublingual gingival administration is in the form of a solid dispersion or suspension as defined herein above. In one embodiments the composition is in the form of a solid dispersion. Such a composition comprises the solid composition of the present invention, e.g. a composition in the form of a powder, and further comprises a bulking agent.

In another embodiment the composition formulated for buccal, sublingual or gingival administration is in the form of a suspension of the solid composition according to the present invention in a liquid carrier as defined hereinabove. According to some embodiments the ACC in the composition in the form of a suspension remains stable for at least 1 hour, least 1, 7, 14 days, 1, 3 or 6 months.

According to some embodiments the composition for administration via inhalation administration further comprises at least one additional active agent.

According to certain embodiments the composition according to the present invention is a solid composition in the form of a dry powder, comprising ACC stabilized by phosphoserine, wherein said ACC is in the form of particles of which at least 90% of the particles have a particle size of 10 μm or less, composition is formulated for buccal or sublingual administration, and the water content of the dry powder is less than 20% w/w. In some embodiment the water content of the dry powder is less than 15% w/w or less than 10% w/w. In some embodiments the dry powder composition comprises about 5 wt % to about 20 wt % or about 5% to about 15 wt % water. According to another embodiment, the composition comprises about 10 wt % to about 20 wt % water. According to another embodiment, at least 90% of the particles have a particle size of 5 μm or less. According to one embodiment such composition is in the form of a suspension in aqueous carrier formulated for administration for inhalation or in the form of a solid dispersion comprising a bulking agent.

According to certain embodiments the composition according to the present invention is a solid composition in the form a dry of powder, comprising ACC stabilized by triphosphate, wherein said ACC is in the form of particles of which at least 90% of the particles have a particle size of 10 µm or less, the water content of the dry powder is less than 20% w/w, the P:Ca molar ratio is about 1:25 to about 1:3, and the composition is formulated buccal or sublingual administration. According to some embodiments the particles have a particle size of 5 µm or less. In other embodiment, the P:Ca molar ratio is about 1:25 to about 1:4. In further embodiment the P:Ca molar ratio is about 1:20 to about 1:5. In another particular embodiment the P:Ca molar ratio is about 1:25 to about 1:5. In further embodiments, the Ca content of such compositions is about 20 wt % to about 38 wt % or about 30 wt % to about 38 wt. In certain embodiments the P:Ca molar ratio is about 1:25 to about 1:3, and the Ca content is about 30 wt % to about 38 wt %. In some embodiments the molar ratio is 1:28 to about 1:3, and the Ca content is about 30 wt % to about 38 wt %. In some embodiments the dry powder composition comprises about 5 wt % to about 20% or about 5% to about 15 wt % water. According to another embodiment, the composition comprises about 10 wt % to about 20 wt % water. According to one embodiment such composition is in the form of a suspension in aqueous carrier formulated for administration for inhalation or in the form of a solid dispersion comprising a bulking agent.

According to any one of the above embodiments, the composition is formulated for gingival administration.

According to any one of the above embodiments the composition is a pharmaceutical composition. Thus it is encompassed by the principles of the present invention that the composition of the present invention is a pharmaceutical composition and/or formulated as a pharmaceutical composition.

According to some embodiment the composition of the present invention is a pharmaceutical composition comprising pharmaceutically acceptable carrier, for use in treating a disease or a condition responsive to a calcium carbonate treatment, wherein said pharmaceutical composition is formulated for an administration selected from the group consisting of administration via inhalation, buccal, gingival and sublingual administration.

The term "pharmaceutical composition" as used herein refers to any composition comprising at least one pharmaceutically active agent, and optionally at least one additional pharmaceutically acceptable carriers, stabilizers, and/or bulking agents.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, and the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate.

According to some embodiments the invention provides a pharmaceutical composition comprising ACC stabilized by at least one stabilizer, as defined hereinabove, wherein the ACC is in the form of particles, and wherein the composition is formulated for an administration selected from the group consisting of administration via inhalation, buccal, sublingual and gingival administration as defined hereinabove. According to some embodiment the ACC is natural ACC. According to another embodiment the ACC is a synthetic ACC stabilized by at least one stabilizer.

Thus according to one embodiment the pharmaceutical composition according to the present invention comprising ACC stabilized by at least one stabilizer selected from the group consisting of polyphosphate, such as pyrophosphate, triphosphate and hexametaphosphate; bisphosphonate, such as alendronic acid, etidronic acid, zoledronic acid and medronic acid; phosphoserine; phosphothreonine; citric acid; and any combination thereof, and the composition is formulated for administration via inhalation administration.

According to some embodiments, the pharmaceutical composition comprises as a stabilizer a polyphosphate. In one embodiment, the polyphosphate is inorganic polyphosphate such as pyrophosphate, triphosphate or hexametaphosphate.

According to some embodiments, the pharmaceutical composition comprises as a stabilizer a bisphosphonate. In other embodiments, the bisphosphonate is selected from alendronic acid, etidronic acid, zoledronic acid and medronic acid.

In one embodiment the pharmaceutical composition formulated for administration via inhalation, for buccal or sublingual administration comprises polyphosphate or bisphosphonate, as defined herein, as a stabilizer as, and the P:Ca molar ratio is as defined hereinabove, e.g. about 1:40 to about 1:1. In a further embodiment, the P:Ca molar ratio is about 1:35 to about 1:2. In certain embodiments, the P:Ca molar ratio is about 1:30 to about 1:3. In other embodiment, the P:Ca molar ratio is about 1:28 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In certain embodiments the P:Ca molar ratio is about 1:25 to about 1:1. In another particular embodiment the P:Ca molar ratio is about 1:25 to about 1:5.

In further embodiments, the Ca content of the pharmaceutical composition is about 20 wt % to 39 wt %, about 30 wt % to about 38 wt %, about 32 wt % to about 38 wt % or about 30 wt % to about 36 wt %. In certain embodiments the P:Ca molar ratio is about 1:40 to about 1:1, and the Ca content is about wt % 20 wt % to about 38 wt %. In some embodiments the molar ratio is 1:28 to about 1:3, and the Ca content is about 30 wt % to about 38 wt %. In another embodiment the molar ratio is 1:25 to about 1:5, and the Ca content is about 30 wt % to about 36 wt %.

According to some embodiments the pharmaceutical composition comprises ACC stabilized by a phosphorylated amino acid. According to further embodiment the stabilizer is phosphoscrine. According to further embodiment the stabilizer is phosphothreoninc.

According to yet another embodiment the pharmaceutical composition comprises ACC stabilized by citric acid.

According to some embodiments the pharmaceutical composition is solid as defined herein above. In particular embodiment the solid pharmaceutical composition is in the form of a dry powder. According to some embodiments the water content of the dry powder does not exceed 30%. In some embodiment the water content of the dry powder is less than 20% w/w, less than 15% w/w or less than 10% w/w. In some embodiments the dry powder pharmaceutical composition comprises about 5 wt % to about 30 wt % or about 5% to about 25 wt % water. According to another embodiment, the pharmaceutical composition comprises about 10 wt % to about 20 wt % water. According to further embodiments, the pharmaceutical composition comprises about 10 wt % to about 25 wt % water.

According to some embodiments the ACC in the pharmaceutical composition is stable for at least 1 month. According to other embodiments the ACC in the pharmaceutical composition is stable for at least 3 months. According to a further embodiment the ACC in the pharmaceutical composition is stable for 6 months. According to certain embodiment the ACC in the pharmaceutical composition is stable for at least 1 year. According to a particular embodiment, the ACC in the pharmaceutical composition is stable to at least 2 years.

According to some embodiments, the pharmaceutical composition comprises less than 30%, crystalline calcium carbonate (CCC) of the total calcium carbonate. In certain embodiments, the pharmaceutical composition comprises less than 25%, less than 20%, less than 15%, less than 10% or less than 5% of CCC of the total calcium carbonate.

According to some embodiments, the pharmaceutical composition is in the form of a solid dispersion or suspension as defined herein above. In one embodiments the pharmaceutical composition is in the form of a solid dispersion. Such a pharmaceutical composition comprises the solid pharmaceutical composition of the present invention, e.g. a pharmaceutical composition in the form of a powder, and further comprises a bulking agent.

In another embodiment, the pharmaceutical composition is in the form of a suspension of the solid pharmaceutical composition according to the present invention in a liquid carrier as defined hereinabove. According to some embodiments the ACC in the pharmaceutical composition in the form of a suspension remains stable for at least 1 hour, least 1, 7, 14 days, 1, 3 or 6 months.

According to some embodiments, the pharmaceutical composition further comprises at least one additional active agent.

According to one embodiment, the pharmaceutical composition is formulated for sublingual administration. According to another embodiment, the pharmaceutical composition is formulated for buccal administration. According to yet another embodiment, the pharmaceutical composition is formulated for administration via inhalation.

The ACC stabilized by at least one stabilizer of the pharmaceutical composition formulated for administration via inhalation is in the form of particles. In certain embodiments, at least 70% or, least 80%, at least 90% or at least 95% of the particles have a particle size of 20 µm or less. In certain embodiments, at least 70%, at least 80%, at least 90% or at least 95% of the particles have a particle size of 15 µm or less. In certain embodiments, at least 70%, at least 80%, at least 90% or at least 95% of the particles have a particle size of 10 µm or less.

In certain embodiments, at least 70% of the particles have a particle size of 5 µm or less. In certain embodiments, at least 80% of the particles have a particle size of 5 µm or less. In certain embodiments, at least 90% of the particles have a particle size of 5 µm or less. In certain embodiments, at least 95% of the particles have a particle size of 5 µm or less.

In certain embodiments, at least 80% or at least 90% of the particles have a particle size of 10-20 µm or less. In certain embodiments, at least 80% or at least 90% of the particles have a particle size of 5-10 µm or less.

According to some embodiments, the pharmaceutical composition formulated for administration via inhalation is in the form of a dry powder configured for dry powder inhalation.

According to another aspect the present invention provides a repository, comprising at least one metered dose of the pharmaceutical composition of the present invention formulated for administration via inhalation, packed in a packaging configured to be used with a dry powder inhaler.

According to certain aspect, the present invention provides an inhaler comprising the repository according to the present invention, configured to allow administration by inhalation of the at least one metered dose of the pharmaceutical composition according to the present invention.

According some other embodiments, the present invention provides a pharmaceutical composition as defined hereinabove, for use in treating a disease or a condition responsive to a calcium carbonate treatment, wherein said pharmaceutical composition is formulated for an administration selected from the group consisting of administration via inhalation, buccal, gingival and sublingual administration.

According certain embodiments, the present invention provides a pharmaceutical composition comprising a composition according to any one of the above embodiments, and a pharmaceutically acceptable carrier, for use in treating a disease or a condition responsive to a calcium carbonate treatment wherein said pharmaceutical composition is formulated for an administration selected from the group consisting of administration via inhalation, buccal, gingival and sublingual administration. According to some embodiment such use further comprises oral administration of a stabilized ACC.

According to some embodiments, the disease or the condition is selected from the group consisting of pain, hyperproliferative diseases, skin afflictions, neurological disorders, immunologic disorders, cardiovascular diseases, pulmonary diseases, nutritional disorders, reproductive disorders, musculoskeletal disorders, infectious diseases and dental diseases. In one particular embodiment the disease is cancer. Thus in one embodiment the composition of the present invention formulated as a pharmaceutical composition or a pharmaceutical composition comprising the composition of the present invention is for use in treating cancer. According to one particular embodiment, the disease or the condition is pain. According to other embodiment, the disease or the condition is cancer. According to some embodiments the cancer is selected from the group consisting of lung, breast and bone cancer. According to another particular embodiment, the disease in an infectious disease.

According to some embodiments, the pharmaceutical composition according to the present invention is formulated for administration via inhalation. According to another embodiments the pharmaceutical composition is formulated for buccal administration.

According to certain embodiments the pharmaceutical composition is formulated for sublingual administration.

According to some embodiments the use comprises administering ACC via inhalation in a dose of 8 ml of about 0.1 to 5% ACC.

According to another embodiment the use comprises administering ACC buccally and/or sublingually in the ACC dose of up to 2000 mg/day of ACC. According to another embodiment the ACC dose is up to 1200 mg/day.

According to another aspect the present invention provides a repository, comprising at least one metered dose of the pharmaceutical composition of the present invention formulated for administration via inhalation, packed in a packaging configured to be used with a dry powder inhaler.

According to certain aspect, the present invention provides an inhaler comprising the repository according to the present invention, configured to allow administration by inhalation of the at least one metered dose of the pharmaceutical composition according to the present invention.

The term "repository" as used herein refers to a storage article, adapted to store one or more items.

The term "metered dose" as used herein refers to a specific amount of a pharmaceutical composition according to the present invention.

According to a further aspect, the present invention provides a method of treating a disease or a condition responsive to a calcium carbonate treatment in a subject in need thereof, comprising administering to the subject an ACC stabilized by at least one stabilizer, via a route of administration selected from administration via inhalation, buccal administration, sublingual administration, gingival administration and any combination thereof.

According to one embodiment the method comprising administering the composition of the present invention. According to another embodiment the method comprising administering the composition according to any one of the above embodiments.

According to certain embodiments the method comprising administering a composition comprising ACC as an active agent, stabilized by at least one stabilizer, wherein the ACC is in the form of particles, and wherein the composition is formulated for an administration selected from the group consisting of administration via inhalation, buccal, sublingual and gingival administration.

According to one embodiment the administration is administration via inhalation. According to another embodiment the administration is buccal administration. According to a further embodiment, the administration is sublingual administration. According to yet another embodiment, the administration is gingival administration. According to some embodiments the administration is via inhalation and by buccal administration. In some embodiments, buccal administration includes sublabial administration.

According to some embodiment the administration further comprises oral administration of a stabilized ACC. According to some embodiments the dose of orally administered ACC is up to 1200 mg/day. It is to be understood that the present invention encompasses methods of administration of compositions comprising ACC via inhalation, wherein said compositions can be administered in combination with ACC administered by other delivery routes, such as, but not limited to buccal, sublingual and/or oral delivery.

According to some embodiments the ACC is a natural or synthetic ACC as defined hereinabove. According to one embodiment the ACC is a natural ACC.

According to another embodiment the ACC is a synthetic ACC. According to some embodiments the ACC is stabilized by at least one stabilizer as defined hereinabove. According to some embodiments the stabilizer is selected from the group consisting of a polyphosphate, bisphosphonate, phosphorylated amino acid, citric acid, and any combination thereof.

According to some embodiments the stabilizer is a polyphosphate or pharmaceutically acceptable salts thereof. According to certain embodiments the polyphosphate is selected from pyrophosphate, triphosphate, and hexametaphosphate.

According to some embodiment the stabilizer is bisphosphonate or pharmaceutically acceptable salts thereof.

According to some embodiments, the composition comprises more than one stabilizer as defined hereinabove.

According to some embodiments the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiment, the P:Ca molar ratio is about 1:25 to about 1:4. In further embodiment the P:Ca molar ratio is about 1:20 to about 1:5. In another embodiment the P:Ca molar ratio is about 1:20 to about 1:6. In a particular embodiment, the P:Ca molar ratio is about 1:15 to about 1:5. In another particular embodiment the P:Ca molar ratio is about 1:25 to about 1:5.

According to some embodiments the calcium content of the administered compositions is as defined hereinabove e.g. about 20 wt % to about 39 wt %. In further embodiments, the Ca content is about 25 wt % to 39 wt %, about 25% to about 38%, about 30 wt % to about 38 wt %, about 32 wt % to about 38 wt % or about 30 wt % to about 36 wt %. In certain embodiments the P:Ca molar ratio is about 1:40 to about 1:1, and the Ca content is about 20 wt % to about 38 wt %°. In some embodiments the molar ratio is 1:28 to about 1:3, and the Ca content is about 30 wt % to about 38 wt %. In another embodiment the molar ratio is 1:25 to about 1:5, and the Ca content is about 30 wt % to about 36 wt %.

According to certain embodiments, the stabilizer is a phosphorylated amino acid. According to one embodiment the phosphorylated amino acid is phosphoserine. According to another embodiment the phosphorylated amino acid is phosphothreonine.

According to some embodiments the stabilizer is an organic acid. According to certain embodiments the organic acid is selected from ascorbic, citric, lactic or acetic acid, oxalic acid, malonic acid, glutaconic acid, succinic acid, maleic acid, lactic acid, aconitic acid, and optionally include compounds having at least two carboxylic groups and molecular weight not larger than 250 g/mol, such as citric acid, tartaric acid, malic acid, etc. According to one particular embodiment the stabilizer is citric acid.

According to any one of the above embodiments, the composition is solid. According to another embodiment such composition is in the form of dry powder.

According to some embodiments the water content of the dry powder does not exceed 30%. Thus in some embodiment the water content of the dry powder is less than 20% w/w, less than 15% w/w or less than 10% w/w. In some embodiments the dry powder composition comprises less than 5% water. In other embodiments the dry powder composition comprises about 5 wt % to about 30 wt % or about 5% to about 25 wt % water. According to another embodiment, the composition comprises about 10 wt % to about 20 wt % water. According to further embodiments, the composition comprises about 10 wt % to about 20 wt % water. In certain embodiments, the composition described above is a dry powder comprising 1 to 99% ACC by weight.

According to some embodiments, the composition comprises less than 30% crystalline calcium carbonate (CCC) of the total calcium carbonate. In certain embodiments, the composition comprises less than 25%, less than 20%, less than 15%, less than 10% or less than 5% of CCC of the total calcium carbonate. According to some embodiment, the composition is stable for at least 1 month. According to other embodiments the composition is stable for at least 3 months. According to a further embodiment the composition is stable for 6 months. According to certain embodiment the composition is stable for at least 1 year. According to a particular embodiment, the composition is stable to at least 2 years.

According to some embodiments the composition according to any one of the above embodiments is in the form of a solid dispersion or a suspension.

In one embodiments the composition is in the form of a solid dispersion. Such a composition comprises the solid composition of the present invention, e.g. a composition in the form of a powder, and further comprises a bulking agent.

In certain embodiments, the composition is in the form of a suspension of the ACC in a liquid carrier. According to some embodiments the liquid carrier comprises at least 80 wt % water. In certain embodiments, the liquid carrier comprises at least 85% water by weight. In certain embodiments, the liquid carrier comprises at least 90% water by weight. In certain embodiments, the liquid carrier comprises at least 95% water by weight or even up to 99.9% water by weight. Optionally the liquid carrier is a philological saline, or any other acceptable pharmaceutical composition for inhalation.

According to one embodiment, the ACC in the composition in the form of a suspension remains stable for at least 1 hour. According to other embodiments the composition is stable for at least 1, 7, 14 days, 1, 3 or 6 months.

According to some embodiments the composition in the form of a suspension as defined hereinabove comprises about 0.01% to 30% w/w of ACC. In further embodiments, the composition in the form of a suspension comprises from about 0.1 wt % to about 5 wt % of ACC. In certain embodiments, the suspension comprises about 1% ACC.

According to any one of the above embodiments, the composition may further comprise at least one additional active agent.

As defined hereinabove the stabilized ACC of the composition formulated for administration via inhalation is in the form of particles. In certain embodiments, at least 70% or, least 80%, at least 90% or at least 95% of the particles have a particle size of 20 µm or less. In certain embodiments, at least 70%, at least 80%, at least 90% or at least 95% of the particles have a particle size of 15 µm or less. In certain embodiments, at least 700%, at least 80%, at least 90% or at least 95% of the particles have a particle size of 10 µm or less.

In certain embodiments, at least 70% of the particles have a particle size of 5 µm or less. In certain embodiments, at least 80% of the particles have a particle size of 5 µm or less. In certain embodiments, at least 90% of the particles have a particle size of 5 µm or less. In certain embodiments, at least 95% of the particles have a particle size of 5 µm or less.

In certain embodiments, at least 80% or at least 90% of the particles have a particle size of 10-20 µm or less. In certain embodiments, at least 80% or at least 90% of the particles have a particle size of 5-10 µm or less.

According to some embodiments the composition formulated for administration via inhalation is in the form of a dry powder configured for dry powder inhalation.

According to some embodiments the composition is formulated for buccal administration. According to another embodiment, the composition is formulation for sublingual administration.

The term "responsive to a calcium carbonate treatment" refers to any disease that may be treated by calcium carbonate. According to one embodiment the disease or the condition is selected from the group consisting of pain, proliferative diseases, skin afflictions, neurological disorders, immunologic disorders, cardiovascular diseases, pulmonary diseases, nutritional disorders, reproductive disorders, musculoskeletal disorders, infectious diseases and dental diseases. According to one particular embodiment, the disease or the condition is pain. According to other embodiment, the disease or the condition is cancer. According to some embodiments the cancer is selected from the group consisting of lung, breast and bone cancer. According to another particular embodiment, the disease in an infectious disease.

Cancer pain is characteristic for people suffering from cancer. In certain other embodiments, the composition according to the invention improves the state of patients with lung cancer. In certain other embodiments, the composition according to the invention mitigates bone pain associated with the proliferative diseases. In certain embodiments, the composition according to the invention improves the wellbeing of patients suffering from malignant diseases. In some embodiments, the composition causes tumors shrinkage and/or relief of at least one cancer symptom at a daily dose of an ACC suspension for inhalation for at least once a day and/or optionally, dry powder inhalation, and/or the administration of ACC for buccal delivery and/or ACC oral dosage form. In certain embodiments, the composition according to the invention causes tumors shrinkage and/or relief of at least one cancer symptom at a daily dose of two portions of 8 ml of 1% ACC suspension for inhalation and/or dry powder inhalation and optionally doses of 600 to 2000 mg ACC for buccal delivery and/or ACC solid oral dosage form.

In certain embodiments, a composition according to the invention improves the state of patients with breast cancer metastasized to other organs, wherein the improvement is selected from the group consisting of shrinkage of the tumors, increase of the bone mass, renewal of nail growth after the radiation therapy, and improved laboratory blood values. Each possibility represents a separate embodiment of the invention.

Treating cancer may include one or more of: reducing a rate of growth of at least one tumor; reducing the size of at least one tumor or even eliminating it; preventing metastasis or reducing its rate or severity; and preventing, reducing or eliminating at least one symptom associated with the disease (e.g. pain).

According to another embodiment the disease is an infectious disease.

According to another embodiment the treating comprises buccal administration of the composition comprising ACC as defined hereinabove. According to certain embodiment the treating comprises sublingual administration the composition comprising ACC as defined hereinabove. According to a further embodiment the treating comprises gingival administration the composition comprising ACC as defined hereinabove. According to some embodiments the treating comprises buccal administration of ACC and administration of ACC via inhalation.

According to some embodiments, the ACC is administered via inhalation in a dose of 8 ml of about 0.1 to 5% ACC.

According to another embodiment the dose of buccally and/or sublingually administered ACC is up to 2000 mg/day of ACC.

According to certain embodiments, the method further comprises oral administration of ACC stabilized by at least one stabilizing agent. According to some embodiments the ACC for oral administration is natural or synthetic ACC.

In a further aspect, the present invention provides use of a composition according to the present invention in the preparation of a medicament formulated for administration via an administration selected from administration via inhalation, buccal, sublingual and gingival administration, for treating a disease or a condition responsive to calcium a carbonate treatment. According to one embodiment the disease or the condition is selected from the group consisting of pain, proliferative diseases, skin afflictions, neurological disorders, immunologic disorders, cardiovascular diseases, pulmonary diseases, nutritional disorders, reproductive disorders, musculoskeletal disorders, infectious diseases and dental diseases. According to one particular embodiment, the disease or the condition is pain. According to other embodiment, the disease or the condition is cancer. According to some embodiments the cancer is selected from the group consisting of lung, breast and bone cancer.

According to one embodiment the administration is administration via inhalation. According to another embodiment the administration is buccal administration. According to a further embodiment, the administration is sublingual administration. According to yet another embodiment, the administration is gingival administration. According to some embodiments the administration is via inhalation and by buccal administration.

According to some embodiment the medicament is administered in conjunction with oral formulation of stabilized ACC.

According to some embodiments the treating comprising administering ACC via inhalation in a dose of 8 ml of about 0.1 to 5% ACC.

As used herein, the term "about", when referring to a measurable value, such as an amount, a temporal duration, and the like is meant to encompass variations of +/−10%, or +/−5%, +/−1%, or even +/−0.1% from the specified value. In one embodiment, the term "comprising" includes "consisting".

The following examples are presented in order to more fully illustrate some embodiments of the invention. They should, in no way be construed, however, as limiting the broad scope of the invention.

EXAMPLES

Materials and Methods

Materials that were used in the experiments are: calcium chloride (78%); sodium carbonate; citric acid. Phosphoserine (PS); Sodium triphosphate (90%); sodium hexametaphosphate (HMP) (90%); ethanol (95%) sodium pyrophosphate (Pyr) (90%); sodium phosphate monobasic (anhydrous), Etidronic acid (ET) (60% aqueous solution); Zoledronic acid (ZA); Medronic acid (MA) and Hydrochloric acid Definition of a Stabilizer Concentration Concentration of a stabilizer in all the examples provided below is defined as follows:

% of a stabilizer=(amount of initially added stabilizer (in g)/amount of initially added CaCl2 (in g))×100

The correlation between different concentrations of stabilizers and the P:Ca molar ratio is summarized in Table 2.

Stability Assessment

The stability of the ACC in the suspension or as a powder was tested by sampling at different time intervals and evaluating the amount of crystalline calcium carbonate as a percent of the initial amount. The amount of crystalline phase of Calcium carbonate in the sample was estimated using X-Ray diffraction (XRD) method.

XRD Collection—Experimental Section

The X-ray data are collected on Panalytical powder diffractometer (Philips 1050/70 or Empyrean), equipped with graphite monochromator on diffracted beam providing Cu—K$_\square$ radiation and operating at V=40 kV, 1=30 mA. Scans are run in a 2$\square$ range of 15-50$\square$ or 24-36° with a step equal to ~0.03°. This interval contains a main peaks of Calcite (reflection (104) at 2 theta deg=29.30±0.2°) and Vaterite (reflections (100), (101) and (102) at 2 theta deg equal to 24.80, 27.0° and 32.7°+0.2° respectively).

The X-ray data are collected on Rigaku powder diffractometer (MiniFlex 600 Benchtop), equipped with graphite monochromator on diffracted beam providing Cu-K$\square$ radiation and operating at V=40 kV, I=15 mA. Scans are run in a 2$\square$ range of 26-34$\square$ with a step equal to ~0.020. This interval contains a main peaks of Calcite (reflection (104) at 2 theta deg=29.3°±0.2°) and Vaterite (reflections (101) and (102) at 2 theta deg equal to 24.80, 27.0° and 32.7°+0.2° respectively).

The samples were compared to a calibration plot built using standard samples comprising known amounts and ratios of amorphous and crystalline (such as Calcite or Vaterite) Calcium Carbonate.

Example 1. Stability of Powder Compositions of ACC Stabilized with Polyphosphates, Phosphate Monobasic or Citric Acid Powder compositions of ACC stabilized by different stabilizers (triphosphate (TP), hexametaphosphate (HMP), pyrophosphate (Pyr), phosphate monobasic (PM) or citric acid (CA)) were prepared. In a typical procedure, a calcium solutions (300 ml of water, 24 g of calcium chloride and a stabilizer) and a carbonate solution (200 m of water and 17.3 g of sodium carbonate) were mixed together to precipitate ACC. A stabilizer solution (100 ml of water and stabilizer; the content of the stabilizers in the calcium and stabilizer solution is presented in Table 1; the correlation between different concentrations of stabilizers and the P:Ca molar ratio is summarized in Table 2) was added to the ACC suspension creating stabilized ACC suspension. The ACC was then filtered using a Buchner funnel, the cake was washed with water. Powder obtained by drying the cake. The stability of ACC in the powder was tested as by XRD as described in material and methods part.

TABLE 1

The content of the stabilizers in different ACC composition

| Composition | 1% TP | 2% TP | 3% TP | 4% TP | 6% TP/ HMP/ Pyr/ CA/ PM | 10% TP/ HMP/ Pyr/ CA/ PM | 15% PM |
|---|---|---|---|---|---|---|---|
| Stabilizer in Calcium solution (g) | 0.12 | 0.24 | 0.36 | 0.48 | 0.72 | 1.2 | 1.8 |
| Stabilizer in Stabilizing solution (g) | 0.12 | 0.24 | 0.36 | 0.48 | 0.72 | 1.2 | 1.8 |

It has been shown that ACC stabilized by more than 1% of triphosphate was stable for at least one months (at the higher concentrations, such as 4% and more, ACC was stable for more than 3 months).

TABLE 2

Correlation between the stabilizer's concentration (in %) and P:Ca molar ratio

| Conc (%) | TP | HMP | Pyr | PM | PS | ET | ZA | MA |
|---|---|---|---|---|---|---|---|---|
| 1 | 1:95 | | | | | | | |
| 2 | 1:48 | 1:39 | 1:40 | | | 1:36 | 1:48 | 1:30 |
| 3 | 1:31 | | | | | | | |
| 4 | 1:24 | 1:20 | 1:26 | | | | | |
| 5 | 1:21 | 1:16 | 1:20 | | 1:26 | 1:14.5 | 1:19 | 1:12 |
| 6 | 1:16 | 1:13 | 1:17 | 1:16 | 1:19* | | | |
| 7 | | | | | | 1:10 | 1:14 | 1:9 |
| 10 | 1:10 | 1:8 | 1:10 | 1:9 | | 1:7 | 1:10 | 1:6 |
| 15 | 1:6 | 1:5.3 | 1:7 | 1:6 | | | | |

*the PS concentration is 6.8%

Example 2. Stability of the Re-Suspended ACC Stabilized by a Combination of Citric Acid with HMP, TP or PS Two powder compositions (referred as 6% HMP-1% CA and 10% HMP-10% CA) of ACC stabilized by citric acid and HMP were prepared as following: the calcium solutions (100 mL of water, 11.76 g of calcium chloride, 0.12 g citric acid, and 0.35 g or 0.59 g of HMP) and carbonate solution (100 ml of water and 8.48 g of sodium carbonate) were mixed together to precipitate ACC. The stabilizer solution (20 ml of water and 0.35 g or 0.59 g HMP) was added to the ACC suspensions creating stabilized ACC suspension (the suspension of 6% HMP-1% CA and of 10% HMP-1% CA comprised 0.7 and 1.18 g HMP, respectively). The ACC was then filtered using a Buchner funnel, the cake was washed with water.

Two powder compositions (referred as 6.8% PS-6% CA-Et-OH and 5% PS-6% CA-Et-OH) of ACC stabilized by citric acid and phosphoserine were prepared as following: the calcium solutions (100 mL of water, 11.76 of calcium chloride, 0.12 g citric acid and 0.8 g or 0.59 g of phosphoserine (for 6.8% PS-6% CA, and 6% PS-6% CA composition, respectively)) and carbonate solution (100 ml of water and 8.48 g of sodium carbonate) were mixed together to precipitate ACC. The stabilizer solution (20 ml of water and 0.59 citric acid) and 50 ml ethanol were added to the ACC suspension creating stabilized ACC suspension. The ACC was then filtered using a Buchner funnel, the cake was washed with ethanol.

The resulted powder was dispersed in 1100 ml of water to obtain a suspension and the stability of the ACC was tested as described in material and methods.

A powder compositions (10% TP-1% CA) of ACC stabilized by citric acid and phosphoserine were prepared as following: the calcium solutions (300 mL of water, 24 g of calcium chloride, 0.24 g citric acid and 1.2 g of triphosphate) and carbonate solution (200 ml of water and 17.3 g of sodium carbonate) were mixed together to precipitate ACC. The stabilizer solution (100 ml of water and 1.2 g triphosphate) was added to the ACC suspension creating stabilized ACC suspension. The ACC was then filtered using a Buchner funnel, the cake was washed with water. The resulted powder was dispersed in 792 ml of water to obtain a suspension and the stability of the ACC was tested as described in material and methods.

A powder compositions (5% PS-5% CA) of ACC stabilized by citric acid and phosphoserine were prepared as following: the calcium solutions (100 mL of water, 11.76 of calcium chloride, 0.12 g citric acid and 0.6 g of phosphoserine and carbonate solution (100 ml of water and 8.48 g of sodium carbonate) were mixed together to precipitate ACC. The stabilizer solution (20 ml of water and 0.48 citric acid) and 50 ml ethanol were added to the ACC suspension creating stabilized ACC suspension. The ACC was then filtered using a Buchner funnel, the cake was washed with ethanol. Powder obtained by drying the cake, 8 g of ACC powder was re-suspended in 792 g water.

All composition were found to be efficient to stabilize ACC for at least a week. HMP-10° %-1% CA and 5% PS-5% CA-Et-OH could stabilize the composition for more than a month with only slight crystallization (no more than 5%).

Example 3. Effect of Different Polyphosphate on Stability of the Re-Suspended ACC Three powder compositions (referred as 10% HMP, 10% Pyr, and 10% TP) were prepared similarly to the teaching of Example 1. The resulted powder was dispersed in 1100 ml water to obtain a suspension and the stability was tested. All compositions preserved stability of ACC for at least 2 weeks with only 15-20% crystallization.

Example 4. Stability of the ACC Stabilized with Bisphosphonates

Several suspensions of stabilized ACC with different content of stabilizers were prepared. In a typical procedure, the calcium solutions (100 mL or 200 mL of water, 12 g of calcium chloride and stabilizer) and carbonate solution (100 ml of water and 8.65 g of sodium carbonate) were mixed together to precipitate ACC. The stabilizer solution (300 ml of water and stabilizer; the content of the stabilizers in calcium and stabilizer solution is presented in Table 3) was added to the ACC suspension creating stabilized ACC suspension. The ACC was then filtered using a Buchner funnel, the cake was washed with water. Suspension obtained by dispersing the cake with water. The resulted powder was dispersed in 1100 ml of water the stability of ACC in a suspension was tested. It has been shown that all compositions preserved ACC in is amorphous state for more than 2 weeks without any sign of crystallization.

TABLE 3

Stabilizer content in different composition

| Composition name | 2% ET | 5% ET | 7% ET | 10% ET | 5% ZA | 10% ZA | 5% MA | 10% MA |
|---|---|---|---|---|---|---|---|---|
| Calcium solution (g) | 0.12 | 0.3 | 0.42 | 0.6 | 0.3 | 0.6 | 0.3 | 0.6 |
| Stabilizing solution (g) | 0.12 | 0.3 | 0.42 | 0.6 | 0.3 | 0.6 | 0.3 | 0.6 |

Example 5. Stability of the Re-Suspended ACC Stabilized with Citric and Etidronic Acids In a typical procedure, the calcium solution contained 100 ml of water, 11.76 g of calcium chloride, 0.12 g of citric acid and 0.59 g of etidronic acid. The carbonate solution contained 100 ml of water and 8.48 g of sodium carbonate. The stabilizing solution contained ml of water and 0.59 g of citric acid. 50 ml of ethanol was used as the organic solvent. The calcium and carbonate solutions were mixed together to precipitate ACC, the stabilizer solution and the ethanol was added to the ACC suspension creating stabilized ACC suspension. The ACC was then filtered using a Buchner funnel, the cake was washed with ethanol. Suspension obtained by dispersing the cake with water. The stability of the ACC was tested. It has been found that the composition preserved ACC in is amorphous state for more than one month without any sign of crystallization Example 6. The Content of a Dried ACC Powder The content of the different compounds such as phosphate atoms and the calcium in the powder preparation of ACC stabilized by different stabilizers and prepared as described in Example 1 was tested using inductivity coupled plasma (ICP) method. The results are summarized Table 4.

TABLE 4

The P:Ca molar ratio, Calcium content and P atoms content in dried ACC compositions determined using ICP.

| Sample | P:Ca molar ratio | Ca wt % | P wt % |
|---|---|---|---|
| ACC-TP1% | 1:95.13 | 37.640 | 0.306 |
| ACC-TP2% | 1:36.95 | 32.625 | 0.682 |
| ACC-TP3% | 1:24.53 | 32.823 | 1.034 |
| ACC-TP4% | 1:19.69 | 34.533 | 1.355 |
| ACC-TP6% | 1:13.09 | 32.686 | 1.930 |
| ACC-TP10% | 1:8.32 | 30.974 | 2.878 |
| ACC-HMP6% | 12.01 | 33.183 | 2.136 |
| ACC-HMP10% | 1:8.25 | 31.995 | 2.998 |
| ACC-PyroP6% | 1:11.63 | 33.225 | 2.209 |
| ACC-PyroP10% | 1:6.62 | 32.907 | 3.842 |

It can be seen that the Ca content of solid powder composition of ACC stabilized with different stabilizers is about 30-40 wt %.

Example 7. Scale-Up Production of ACC-TP10% Powder

In a typical procedure, the calcium solution contained 11 L of water, 1.2 kg of calcium chloride and 60 g of triphosphate. The carbonate solution contained 10 L of water and 864 g of sodium carbonate. The stabilizing solution contained 1 L of water and 60 g of triphosphate. The calcium and carbonate solutions were mixed together to precipitate ACC, the stabilizer solution and was added to the ACC suspension creating stabilized ACC suspension. The ACC was then filtered using a nutsche filter funnel, the cake was washed with water. Powder obtained by drying the cake. The stability of the resulted powder is presented Table 5.

TABLE 5

Stability of ACC-TP10% powder

| Sample | Day | % ACC | % CCC |
|---|---|---|---|
| ACC-TP10% | 3 | 95 | 5 |
| ACC-TP10% | 274 | 90 | 10 |

Example 8. Water Content of a Solid ACC Stabilized by Different Stabilizers

A thermogravimetric analysis was used to determine a water content of solid ACC preparations stabilized with different stabilizers. TGA Q500 V20.13/Universal V4.5A TA instrument was used with the following heating program: RT-1000° C., heating rate: 10° C./min. $N_2$ flow: 80 ml/min. sample weight: ~10-15 mg, one repetition.

In the TGA curves two apparent weight losses processes are found: the first could be assigned to the water released from RT to about 300° C. and the second at a temperature range of about 500-800° C. to the decomposition of calcium carbonate. It could be estimated that the water content in the ACC-TP samples was about 17-18% The results are summarized in Table 6.

TABLE 6

Water content of a solid ACC stabilized as measured by TGA

| Sample | Loss On Drying by TGA |
|---|---|
| ACC-TP2% | 18.0% |
| ACC-TP3% | 17.3% |
| ACC-TP4% | 18.3% |
| ACC-TP6% | 18.0% |
| ACC-Pyro-P6% | 17.4% |
| ACC-Pyro-P10% | 15.4% |
| ACC-HMP6% | 17.2% |

Example 9. Preparation of Powder Composition Formulated for Administration Via Inhalation ACC for dry powder inhalation is a dry powder comprising ACC having particle size that is less than 10 μm or even less than 5 μm for at least 90% of the particles.

Preparation of ACC for dry powder was performed by drying caked matter produced by any of the procedures discussed above, e.g. in Example 1, and milling such that at least 90% of the particles has a particle size of 5 μm or less. Other known methods for preparing ACC formulations may also be applied. Optionally, ACC is prepared by drying and milling naturally occurring ACC (for example a crustacean gastrolith).

Example 10. Inhalation Toxicity Study

ACC is highly soluble and consists of nano-particles in the range of 40-100 nm. These unique properties of ACC allow its unique administration via inhalation, which provides pulmonary topical action and/or systemic action and thus can be an efficient route for ACC entrancing the blood system. Such administration may be useful in the treatment of various diseases including but not limiting cancer.

The principle of the study was to test the toxicity of ACC chronic administration by inhalation on healthy naïve mice. Mice were subjected to ACC inhalation twice a day, 5 days per week for 4 weeks. This is common and sufficient for toxicity evaluation. The study examined both male and female mice (total of 12 mice in a group). Three different concentrations of ACC were tested (0.5%, 1% and 2%) on three different mice groups. Control group was subjected to saline inhalation only, the vehicle of the ACC suspension.

Materials & Methods 25, 50 or 100 mg of ACC were mixed with saline to create concentrations of 0.5%, 1%, 2% w/w of ACC inhalation suspension, respectively. ACC aerosols were generated using a jet nebulizer (PariBoy) and delivered, while keeping a specific aerosol concentration, into a sealed plastic cages that contained the tested mice group. In the pneumatic nebulization aerosols are generated by standing waves. This is the result of applying air stream through medication solutions. Aerosols were diluted with supply air until the desired chamber aerosol concentrations were achieved. Specifically, 5 ml of ACC suspension were loaded in the nebulizer operating at an air flow rate of 4 l/min. Maximum operation period was set to 20 min. Temperatures were monitored continuously with an acceptable range of 18-22° C.

The end points of the study were based on differences in clinical signs scoring, mice mortality, mice body weight, mice clinical blood analysis (general and biochemical), organ gross pathology and Lung histopathology.

Results

No significant changes were found in the ACC agglomerates particles size i.e. their Mass Median Aerodynamic Diameter (MMAD) along the inhalation session. 1% ACC aerosols MMAD median was found to be <1 μm where the 2% ACC aerosols MMAD median was found <3 μm, at the beginning and at the ending of the inhalation session (Tables 7 and 8).

TABLE 7

Characterization of 1% nebulized ACC.

| Initiation of Nebulization | | End of Nebulization | |
|---|---|---|---|
| Aerosol particle size (μm) | In size range (%) | Aerosol particle size (μm) | In size range (%) |
| 0.1-1.0 | 51.34 | 0.1-1.0 | 65.54 |
| 1.0-2.0 | 25.43 | 1.0-2.0 | 22.49 |
| 2.0-3.0 | 9.41 | 2.0-3.0 | 6.87 |
| 3.0-4.0 | 6.43 | 3.0-4.0 | 3.39 |
| 4.0-5.0 | 3.21 | 4.0-5.0 | 1.13 |

TABLE 8

Characterization of 2% nebulized ACC.

| Initiation of Nebulization | | End of Nebulization | |
|---|---|---|---|
| Aerosol particle size (μm) | In size range (%) | Aerosol particle size (μm) | In size range (%) |
| 01-1.0 | 35.60 | 0.1-1.0 | 11.43 |
| 1.0-2.0 | 31.85 | 1.0-2.0 | 25.50 |
| 2.0-3.0 | 12.57 | 2.0-3.0 | 30.28 |
| 3.0-4.0 | 8.19 | 3.0-4.0 | 21.47 |
| 4.0-5.0 | 4.13 | 4.0-5.0 | 9.72 |

No physical nor behavioral changes were observed and no mortality was found in any of the mice groups all through the study duration. Additionally, all groups gained weight during the study period and demonstrated similar body weight balances.

All blood clinical chemistry results (Glucose, urea nitrogen, creatinine, total protein, albumin, alkaline phosphatase (AP), aspartate transaminase (ASP), alanine transaminase (ALT), calcium, sodium, potassium, phosphorous, magnesium and cholinesterase) were found to be in the normal range. In addition, when comparing each group to the control group no significant difference was found by statistical T-test analysis, all P values >0.05.

No pathological signs were detected at the gross pathology examination. In addition, no statistical significant differences were found (at P values of >0.05) when comparing the wet weights of mice internal organs (heart, lung, liver, spleen and kidney) to the control group.

No suggested treatment-related lesion was seen in any of the organs examined by histopathology. Incidental lesions were seen in the liver and kidneys, all known to occur spontaneously in untreated mice. Artifact Intra-alveolar hemorrhages were detected in the mice lungs due to the method of animal termination (neck dislocation). These are not considered as related to the test compound administration. In addition, other signs of diffuse alveolar damage (DAD) such as pulmonary edema, hyaline membranes and alveolar wall destructions were not observed.

Conclusion

From all of the above it can be concluded that ACC aerosol inhalations did not induce any observed toxicity and can be used as an administration route of ACC.

Example 11. Buccal Administration of ACC to a Cancer Patient

A woman presented with a cyst at the base of her tongue was diagnosed as malignant neoplasm of base of tongue. The cyst was removed for biopsy and diagnosed as adenoid cystic carcinoma. The recommended treatment was surgery.

The woman began taking ACC via buccal and/or oral administration. She took 200 mg twice a day (totaling 400 mg per day). ACC was delivered in the form of a tablet (Density™, Amorphical Ltd., Israel) which was chewed for about 5 minutes. Any remaining material was swallowed (optionally aided by some drink or food). No other treatment was provided in this period.

After a period of 2 months of ACC administration, in preparation for surgery, it was found and confirmed by biopsy that the tumor disappeared.

Example 12. ACC Administration Via Inhalation Combined with an Oral Administration to Cancer Patients A single arm, open label, compassionate clinical supportive care study to assess the welfare improvement of terminally ill, late advanced, solid cancer patients (with or without lung involvement) by Amorphous Calcium Carbonate (ACC) treatment, administered orally and concomitantly by inhalation is carried out.

Study Population:

20 subjects with solid malignancies, with or without lung metastases, who failed anti-cancer treatment are enrolled.

Dosage Regiment

Oral Dosage Form

DENSITY is formulated as a caplet containing ACC, as well as Cellulose Microcrystalline, Plasdone K-25, Stearic Acid, and Magnesium Stearate as inactive excipients.

Each DENSITY caplet contains 666 mg ACC as API (i.e. Amorphous $CaCO_3$+Aerosil+drug substance stabilizers) which corresponds to 500 mg $CaCO_3$, and equivalent to 200 mg elemental calcium (hereinafter the dose refers to the amount of elemental calcium). Up to nine DENSITY tablets are administered per day for a maximal calcium dose of 1.800 mg/day.

Inhalation Dosage Form

Inhalation formulation is formed from 1% ACC (i.e. 0.3% calcium)+water for injection, as a sterile suspension (8 mL, twice daily).

All subjects start at a DENSITY dose of 600 mg per day and are escalated to a total daily dose of up to 1,800 mg and Inhaled 1% ACC in 8 mL water, twice daily.

Study Procedures

Twenty (20) subjects diagnosed with late stage solid cancer (with or without lung involvement) who failed other anti-cancer treatment are enrolled and administered with both oral ACC up to 1,800 mg in the form of DENSITY in addition to an inhaled solution of 1% ACC stabilized with a polyphosphate.

Starting Dose: Oral ACC 600 mg (3 tablets, one tablet taken three times a day) scaled up by 200 mg every second day until reaching a maximum dose of 1,800 mg. ACC Inhaled; 1% ACC in 8 mL saline once daily and escalated after 3 days to a maximum dose of Inhaled 1% ACC in 8 mL saline twice daily The calcium levels are evaluated using serum calcium corrected for albumin (CA) value tests before each dose escalation.

Endpoints

Compassionate clinical supportive care program evaluating the improvement of subject's welfare as determined by assessing:

Reduction in pain based on VAS score

Opiate withdrawal by dose and/or numbers of analgesic products

Functional improvement based on ECOG PS

Survival as compared to physician estimation or hospice historical data

Change in arterial oxygen saturation as determined by pulse oximeter

Evaluation Endpoints (Safety):

Percent of subjects with hypercalcemia DLTs per dose

Percent of subjects with any DLTs per dose

Vital Signs

Height and weight are measured as per protocol. (Insert the position and times when such evaluations are performed—e.g. X minutes after rest).

Throughout all study phases, vital signs (temperature, peripheral arterial blood pressure, heart rate and respiratory rate), are obtained after the subject has rested for 5 minutes. Temperature is obtained by thermometer throughout all study phases.

Peripheral arterial blood pressure (systolic, diastolic) is obtained by sphygmomanometry throughout all study phases.

Heart rate is obtained using calibrated standard measuring devices.

Respiratory rate is obtained by observing chest excursions for a minimum of 30 seconds.

The physical examination is conducted on all major organ systems, excluding rectal and pelvic examinations. Weight and height is measured and recorded as per protocol.

The Investigator will use clinical judgment when determining the clinical significance of any physical examination finding.

Physical Examination

A physical examination is performed and documented by the investigator or a qualified designee. Any abnormal findings, assessed by the investigator as clinically significant, should be recorded in the relevant CRF modules (e.g. adverse event, medical history)

In monitoring the patient for positive and negative results one or more of the following is accepted as improvement:

Functional improvement based on ECOG PS;

Prolonged survival as compared to at least one of physician estimation or hospice historical data Increase in arterial oxygen saturation as determined by pulse oximeter Pain reduction (VAS scale), in at least one of intensity, frequency and duration.

In selecting an ACC dosing regimen, blood calcium measurements or changes therein may be used as a consideration according to which to adjust a dosage for a given patient. For example an increase or even development of hypercalcemia may cause a reduction of daily dosage and/or in spreading the ACC dose to smaller doses taken more often.

Example 13. ACC Administration by Inhalation to a Cancer Patient

A 43-year-old woman was diagnosed with advanced breast cancer with metastases, estimated to have existed about 3-4 years before diagnosis.

Three and a half years after diagnosis, and despite treatment, three tumors were found in one of her lungs and a plurality of smaller tumors was present in the other lung. The woman suffered from pelvis fractures, a fractured elbow, a dispersed tumor in her lungs and head. She received radiation therapy for the head tumor.

In addition, she suffered severe pain in her lungs and great difficulty in basic functions, limited breathing capability, reduced speech and difficulty moving.

She was then hospitalized for severe pain and eventually released from hospital with the purpose of receiving no treatment, and her life expectancy was limited to two to six weeks. At this time her blood oxygen saturation was about 80% and she was constantly provided with an oxygen mask, still being breathless, with reduced speech and motion and suffering from severe pain.

The woman started an oral therapy of 2 pills 3 times a day, totaling 1200 mg ACC, with commercially available ACC (Density™, by Amorphical Ltd. Israel. Each DENSITY caplet contains 666 mg (Amorphous $CaCO_3$+Aerosil+drug substance stabilizers) which corresponds to 500 mg $CaCO_3$, and equivalent to 200 mg elemental calcium.

for pain reduction. After several days of such oral therapy, the patient also began inhalation of an ACC suspension. Inhalation was performed twice daily, with 8 ml of 1% ACC prepared with polyphosphate suspended in sterile water. No other anti-cancer treatment was provided during ACC administration.

Within several days from the beginning of ACC inhalation, there was dramatic pain reduction. Within several weeks from the beginning of inhalation (the maximal life expectancy that was predicted for this patient), blood oxygen saturation was near normal (95%) without an oxygen mask and speech capability was greatly improved. It also became much easier for her to change between sitting and reclining postures, sitting to standing, etc. At the same time, the pain in her chest disappeared completely.

Within two months from the beginning of ACC treatment, the patient regained her ability to walk. In imaging, 2 of the 3 large tumors in one lung were no longer detectable, and the other reduced in size. In the other lung, all tumors were dramatically reduced.

While the present invention has been described with reference to certain embodiments and Examples, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The invention claimed is:

1. A method of treating a disease or a condition responsive to a calcium carbonate treatment in a subject in need thereof, the method comprising:
administering to the subject an amorphous calcium carbonate (ACC) as an active agent stabilized by at least one stabilizer via a route of administration selected from administration via inhalation, buccal administration, sublingual administration, gingival administration, and any combination thereof.

2. The method of claim 1, wherein administering comprises administering to the subject a composition comprising:
the ACC as the active agent, stabilized by at least one stabilizer;
wherein the ACC is in the form of particles; and
wherein the composition is formulated for at least one administration mode selected from the group consisting of inhalation administration, buccal administration, sublingual administration, and gingival administration.

3. The method of claim 1, wherein the disease or the condition is selected from the group consisting of pain, cancer, hyperproliferative diseases, skin afflictions, neurological disorders, immunologic disorders, cardiovascular diseases, pulmonary diseases, nutritional disorders, reproductive disorders, musculoskeletal disorders, infectious diseases, and dental problems.

4. The method of claim 3, wherein the disease or the condition is selected from the group consisting of pain, cancer, and infectious disease.

5. The method of claim 1, wherein administering the ACC includes administering the ACC in a dose selected from 8 ml of 0.1 to 5% stabilized ACC via inhalation and up to 2000 mg/day of ACC via buccal and/or sublingual administration.

6. The method of claim 1, wherein the ACC is a natural ACC or synthetic ACC.

7. The method of claim 1, wherein the ACC is a synthetic ACC, and wherein the stabilizer is selected from the group consisting of a polyphosphate, phosphorylated amino acid, bisphosphonate, citric acid, tartaric acid, and any combination thereof.

8. The method of claim 7, wherein the polyphosphate is selected from the group consisting of triphosphate, pyrophosphate, and hexametaphosphate; wherein the phosphorylated amino acid is phosphoserine or phosphothreonine; and wherein the bisphosphonate is selected from the group consisting of alendronate, etidronic acid, zoledronic acid and medronic acid.

9. The method of claim 7, wherein the stabilizer is polyphosphate or bisphosphonate, and wherein a molar ratio between P atoms of the stabilizer and Ca atoms of the ACC is about 1:90 to 1:1.

10. The method of claim 7, wherein the stabilizer is polyphosphate or bisphosphonate, and wherein a molar ratio between P atoms of the stabilizer and Ca atoms of the ACC is about 1:30 to about 1:3.

11. The method of claim 7, wherein the stabilizer is polyphosphate or bisphosphonate, and wherein a molar ratio between P atoms of the stabilizer and Ca atoms of the ACC is 1:25 to about 1:5.

12. The method of claim 2, wherein the composition is in the form of a dry powder.

13. The method of claim 12, wherein the dry powder has a water content that does not exceed 30% w/w.

14. The method of claim 2, wherein the composition is a solid dispersion.

15. The method of claim 14, wherein the solid dispersion includes a bulking agent.

16. The method of claim 2, wherein the composition is in the form of a suspension of ACC in a liquid carrier.

17. The method of claim 16, wherein the composition is characterized by at least one of the following:
(i) the liquid carrier includes at least 80 wt % water;
(ii) the ACC remains stable for at least 1 hour; or
(iii) the composition includes from about 0.1% to about 30% w/w ACC.

18. The method of claim 2, wherein the composition further comprises at least one additional active agent.

19. The method of claim 2, wherein the composition is formulated for administration via inhalation.

20. The method of claim 19, wherein at least 70% of the particles have a particle size of 20 µm or less.

21. The method of claim 19, wherein the composition is in the form of a dry powder configured for dry powder inhalation.

* * * * *